(12) United States Patent
Ottens et al.

(10) Patent No.: US 8,557,526 B2
(45) Date of Patent: Oct. 15, 2013

(54) SYNAPTOTAGMIN AND COLLAPSIN RESPONSE MEDIATOR PROTEIN AS BIOMARKERS FOR TRAUMATIC BRAIN INJURY

(75) Inventors: Andrew K. Ottens, Glen Allen, VA (US); Firas H. Kobaissy, Gainesville, FL (US); Ka-Wang (Kevin) Wang, Gainesville, FL (US); Ronald L. Hayes, Gainesville, FL (US); Zhiqun Zhang, Gainesville, FL (US); Ming Chen Liu, Gainesville, FL (US); Monika Oli, Gainesville, FL (US)

(73) Assignees: University of Florida Research Foundation, Inc., Gainesville, FL (US); Banyan Biomarkers, Inc., Alachua, FL (US)

( * ) Notice: Subject to any disclaimer, the term of this patent is extended or adjusted under 35 U.S.C. 154(b) by 78 days.

(21) Appl. No.: 12/535,960

(22) Filed: Aug. 5, 2009

(65) Prior Publication Data

US 2010/0047817 A1    Feb. 25, 2010

Related U.S. Application Data

(63) Continuation-in-part of application No. PCT/US2008/001644, filed on Feb. 6, 2008.

(60) Provisional application No. 60/888,432, filed on Feb. 6, 2007.

(51) Int. Cl.
*G01N 33/53* (2006.01)
*G01N 33/566* (2006.01)

(52) U.S. Cl.
USPC .......................................... 435/7.1; 436/501

(58) Field of Classification Search
None
See application file for complete search history.

(56) References Cited

U.S. PATENT DOCUMENTS

| | | | |
|---|---|---|---|
| 5,118,606 A | 6/1992 | Lynch | |
| 5,354,662 A | 10/1994 | Stone | |
| 5,536,639 A | 7/1996 | Siman | |
| 7,396,654 B2 * | 7/2008 | Hayes et al. | 435/7.92 |
| 2005/0037430 A1 | 2/2005 | Khan | |
| 2005/0260697 A1 * | 11/2005 | Wang et al. | 435/23 |

OTHER PUBLICATIONS

Zhiqun Zhang et al., 2007, J. Neurotrauma, vol. 24, No. 3, pp. 460-473.*
Kobeissy et al., 2006, MCP, vol. 5, No. 10, pp. 1887-1898.*
Siman et al., 2004, Neurobiology of Disease, vol. 16, 311-20.*
Liu et al, Biochem. J. 2006, 394:715-25.*
Kobeissy, F. H. at al. "Novel Differential Neuroproteomics Analysis of Traumatic Brain Injury in Rats" *Molecular & Cellular Proteomics*, 2006, pp. 1887-1898, vol. 5.
Jin, K. et al. "Evidence for stroke-induced neurogenesis in the human brain" *PNAS*, Aug. 29, 2006, pp. 13198-13202, vol. 103, No. 35.
Czech, T. et al. "Reduction of Hippocampal Collapsin Response Mediated Protein-2 in Patients with Mesial Temporal Lobe Epilepsy" *Neurochemical Research*, Dec. 2004, pp. 2189-2196, vol. 29, No. 12.
Siman, R. et al. "Proteins released from degenerating neurons are surrogate markers for acute brain damage" *Neurology of Disease*, 2004, pp. 311-320, vol. 16.
Inagaki, N. et a/. "CRMP-2 induces axons in cultured hippocampal neurons" *Nature Neuroscience*, Aug. 2001, pp. 781-782, vol. 4, No. 8.
Dutta, S. et al. "Selective Release of Calpain Produced αll-Spectrin (α-Fodrin) Breakdown Products by Acute Neuronal Cell Death" *Journal of Biological Chemistry*, May 2002, pp. 785-791, vol. 383.
Siman, R. et al. "Excitatory Amino Acids Activate Calpain I and Induce Structural Protein Breakdown In Vivo" *Neuron*, Jun. 1988, pp. 279-287, vol. 1.

* cited by examiner

*Primary Examiner* — Olga N Chernyshev
(74) *Attorney, Agent, or Firm* — Saliwanchik, Lloyd & Eisenschenk

(57) ABSTRACT

Collapsin response mediator proteins (CRMPs) decreased in tissue and increased in biological fluids after neural injury from traumatic brain injury (TBI). Significant decreases of CRMP1, CRMP2, CRMP4 and CRMP5 were accompanied by the appearance of distinct 58 kDa (CRMP-2) or 55 kDa (CRMP-4) breakdown products from proteolytic cleavage by calpain. Synaptotagmin breakdown products were also associated with TBI and could be detected along with intact protein in human cerebral spinal fluid (CSF). Both biomarkers were detected in human biofluid and related to recovery from traumatic brain injury.

15 Claims, 15 Drawing Sheets

SEQUENCE LISTING

<160> NUMBER OF SEQ ID NOS: 18

<210> SEQ ID NO 1
<211> LENGTH: 9
<212> TYPE: PRT
<213> ORGANISM: Homo sapiens

<400> SEQUENCE: 1

Thr Met Lys Asp Gln Ala Leu Lys Asp
1               5

<210> SEQ ID NO 2
<211> LENGTH: 12
<212> TYPE: PRT
<213> ORGANISM: Homo sapiens

-continued

```
<400> SEQUENCE: 2

Leu Gly Lys Thr Met Lys Asp Gln Ala Leu Lys Asp
1               5                   10

<210> SEQ ID NO 3
<211> LENGTH: 9
<212> TYPE: PRT
<213> ORGANISM: Homo sapiens

<400> SEQUENCE: 3

Lys Thr Met Lys Asp Gln Ala Leu Lys
1               5

<210> SEQ ID NO 4
<211> LENGTH: 21
<212> TYPE: PRT
<213> ORGANISM: Homo sapiens

<400> SEQUENCE: 4

Ala Ile Asn Met Lys Asp Val Lys Asp Leu Gly Lys Thr Met Lys Asp
1               5                   10                  15

Gln Ala Leu Lys Asp
            20

<210> SEQ ID NO 5
<211> LENGTH: 11
<212> TYPE: PRT
<213> ORGANISM: Homo sapiens

<400> SEQUENCE: 5

Ala Ile Asn Met Lys Asp Val Lys Asp Leu Gly
1               5                   10

<210> SEQ ID NO 6
<211> LENGTH: 11
<212> TYPE: PRT
<213> ORGANISM: Homo sapiens

<400> SEQUENCE: 6

Pro Gly Gly Arg Ala Asn Ile Thr Ser Leu Gly
1               5                   10

<210> SEQ ID NO 7
<211> LENGTH: 77
<212> TYPE: PRT
<213> ORGANISM: Homo sapiens

<400> SEQUENCE: 7

Lys Ala Arg Ser Arg Leu Ala Glu Leu Arg Gly Val Pro Arg Gly Leu
1               5                   10                  15

Tyr Asp Gly Pro Val Cys Glu Val Ser Val Thr Pro Lys Thr Val Thr
                20                  25                  30

Pro Ala Ser Ser Ala Lys Thr Ser Pro Ala Lys Gln Gln Ala Pro Pro
            35                  40                  45

Val Arg Asn Leu His Gln Ser Gly Phe Ser Leu Ser Gly Ala Gln Ile
        50                  55                  60

Asp Asp Asn Ile Pro Arg Arg Thr Thr Gln Arg Ile Val
65                  70                  75

<210> SEQ ID NO 8
<211> LENGTH: 20
<212> TYPE: PRT
<213> ORGANISM: Homo sapiens
```

<400> SEQUENCE: 8

Lys Ala Arg Ser Arg Leu Ala Glu Leu Arg Gly Val Pro Arg Gly Leu
1               5                   10                  15

Tyr Asp Gly Pro
            20

<210> SEQ ID NO 9
<211> LENGTH: 18
<212> TYPE: PRT
<213> ORGANISM: Homo sapien

<400> SEQUENCE: 9

Leu Arg Gly Val Pro Arg Gly Leu Tyr Asp Gly Pro Val Cys Val Ser
1               5                   10                  15

Val Thr

<210> SEQ ID NO 10
<211> LENGTH: 22
<212> TYPE: PRT
<213> ORGANISM: Homo sapiens

<400> SEQUENCE: 10

Thr Pro Lys Thr Val Thr Pro Ala Ser Ser Ala Lys Thr Ser Pro Ala
1               5                   10                  15

Lys Gln Gln Ala Pro Pro
            20

<210> SEQ ID NO 11
<211> LENGTH: 10
<212> TYPE: PRT
<213> ORGANISM: Homo sapiens

<400> SEQUENCE: 11

Lys Ala Arg Ser Arg Leu Ala Glu Leu Arg
1               5                   10

<210> SEQ ID NO 12
<211> LENGTH: 9
<212> TYPE: PRT
<213> ORGANISM: Homo sapiens

<400> SEQUENCE: 12

Leu Arg Gly Val Pro Arg Gly Leu Tyr
1               5

<210> SEQ ID NO 13
<211> LENGTH: 9
<212> TYPE: PRT
<213> ORGANISM: Homo sapiens

<400> SEQUENCE: 13

Thr Pro Lys Thr Val Thr Pro Ala Ser
1               5

<210> SEQ ID NO 14
<211> LENGTH: 12
<212> TYPE: PRT
<213> ORGANISM: Homo sapiens

<400> SEQUENCE: 14

Leu Glu Asp Gly Thr Leu His Val Thr Glu Gly Ser
1               5                   10

```
<210> SEQ ID NO 15
<211> LENGTH: 10
<212> TYPE: PRT
<213> ORGANISM: Homo sapiens

<400> SEQUENCE: 15

Gly Val Pro Arg Gly Leu Tyr Asp Gly Pro
1               5                   10

<210> SEQ ID NO 16
<211> LENGTH: 10
<212> TYPE: PRT
<213> ORGANISM: Homo sapiens

<400> SEQUENCE: 16

Asp Gly Pro Val Cys Glu Val Ser Val Thr
1               5                   10

<210> SEQ ID NO 17
<211> LENGTH: 13
<212> TYPE: PRT
<213> ORGANISM: Homo sapiens

<400> SEQUENCE: 17

Ser Ala Lys Thr Ser Pro Ala Lys Gln Gln Ala Pro Pro
1               5                   10

<210> SEQ ID NO 18
<211> LENGTH: 73
<212> TYPE: PRT
<213> ORGANISM: Homo sapiens

<400> SEQUENCE: 18

Arg Leu Ala Glu Leu Arg Gly Val Pro Arg Gly Leu Tyr Asp Gly Pro
1               5                   10                  15

Val Cys Glu Val Ser Val Thr Pro Lys Thr Val Thr Pro Ala Ser Ser
            20                  25                  30

Ala Lys Thr Ser Pro Ala Lys Gln Gln Ala Pro Pro Val Arg Asn Leu
        35                  40                  45

His Gly Ser Gly Phe Ser Leu Ser Gly Ala Gln Ile Asp Asp Asn Ile
    50                  55                  60

Pro Arg Arg Thr Thr Gln Arg Ile Val
65                  70
```

SYNAPTOTAGMIN AND COLLAPSIN RESPONSE MEDIATOR PROTEIN AS BIOMARKERS FOR TRAUMATIC BRAIN INJURY

CROSS-REFERENCE TO RELATED APPLICATIONS

This application is a continuation-in-part of International Application No. PCT/US2008/001644, filed Feb. 6, 2008, which claims priority from U.S. Provisional Application Ser. No. 60/888,432, filed Feb. 6, 2007, now abandoned.

This invention was made with government support by the Department of Defense (DOD) grant Pe DAMDI 7-03-1-0066, and the National Institutes of Health (NIH) grants R01 NS39091 and R01 N S40182. The government has certain rights in the invention.

BACKGROUND OF THE INVENTION

1. Field of the Invention

The invention concerns neuroprotein changes associated with neurological damage and particularly to assays and diagnosis relating to traumatic brain injury.

2. Description of Background Art

The incidence of traumatic brain injury (BI) in the United States is conservatively estimated to be more than 2 million persons annually with approximately 500,000 hospitalizations. Of these, about 70,000 to 90,000 head injury survivors are permanently disabled. The annual economic cost to society for care of head-injured patients is estimated at $25 billion. Assessment of pathology and neurological impairment immediately after TBI is crucial for determination of appropriate clinical management and for predicting long-term outcome.

The outcome measures most often used in head injuries are the Glasgow Coma Scale (GCS), the Glasgow Outcome Scale (GOS), computed tomography and magnetic resonance imaging (MRI) to detect intracranial pathology. However, despite dramatically improved emergency triage systems based on these outcome measures, most TBI patients suffer long term impairment and a large number of TBI survivors are severely affected despite predictions of "good recovery" on the GOS. In addition, CT and MRI are expensive and cannot be rapidly employed in an emergency room environment. Moreover, in austere medical environments associated with combat, accurate diagnosis of TBI would be an essential prerequisite for appropriate triage of casualties.

The neural pathways of a mammal are particularly at risk if neurons are subjected to mechanical or chemical trauma or to neuropathic degeneration sufficient to put the neurons that define the pathway at risk of dying.

TBI represents a major central nervous system (CNS) disorder without any clinically proven therapy. Evidence of axonal damage following TBI is recognized and prolonged traumatic axonal injury (TAI) is a universal and critical event following TBI, as well as a key predictor of clinical outcome. Integrity of myelin sheaths, which surround axons, is not well studied, but has been reported to increase after TBI in humans.

Collapsin response mediator protein-2 (CRMP-2), also known as CRMP62, TOAD-64 (turned on after division 64 kDa), Ulip-2 (Unc-33-like phosphoprotein) and DRP2 (dihydropyrimidinase-related phosphoprotein), is one of at least five members (CRMP-1-5) of the CRMP family. It was first identified as an intracellular component of the extracellular semaphoring 3A (Sema 3A) signal transduction pathway in chick dorsal root ganglia (DRG), which was known as an inhibitor protein for axonal guidance. CRMP-2 is a developmentally regulated protein that is exclusively expressed in the nervous system. It is concentrated in growing axons, dendrites, and the cytoplasm of differentiating neurons.

A lesser amount of CRMP2 has been detected in select adult neurons, such as the pyramidal cells of the hippocampus, Purkinje cells of the cerebellum and sensory neurons of the DRG. CRMP-2 appears to have an important role in the determination of axon and dendrite integrity. Inagaki, et al. (2001) initially found enrichment of CRMP2 in the distal parts of growing hippocampal axons but later discovered that over-expression of full-length CRMP2 induced formation of multiple axons and elongation of the primary axon, while the dominant-negative form of CRMP2 inhibited axon formation in hippocampal cell culture. The presence of CRMP2 fosters conversion of immature neurites and preexisting dendrites into axons.

Non-phosphorylated CRMP2 enriches in axonal growth cones, promotes axon outgrowth, and induces formation of multiple axon-like neurites. GSK-3-phosphorylated CRMP2 at Thr-514 inactivates CRMP2 and thereby inhibits neuronal polarization. Neurotrophin-3 (NT-3) and brain-derived neurotrophic factor (BDNF) inhibits GSK-3b via the phosphatitylinositol-3-kinase (PI3-kinase)/Akt (also known as PKB) pathway and thereby reduces phosphorylation levels of CRMP2 at Thr-514, leading to axon elongation and branching.

A high degree of phosphorylation is associated with neurofibrillary tangles in Alzheimer's diseased brains, suggesting that CRMP2 may play a role in neurodegeneration. A growing body of evidence suggests that CRMP2 may also participate in the pathophysiology of other neurological disorders. Decreased expression of CRMP2 has been reported in fetal brains with Down's syndrome, patients with mesial temporal lobe epilepsy, focal ischemic rat brain and in the frontal cortex of patients who suffer from psychiatric disorders such as schizophrenia, bipolar, or major depression disorders. In contrast, an increase in CRMP2 is observed after chronic anti-depressant treatment in rat hippocampus. CRMP2 has also been reported to mediate axonal damage and neuronal death via a semaphorine-CRMP pathway.

The role, if any, of synaptic dysfunction in relation to neural injury or brain trauma is not well understood. Synaptotagmins are important calcium sensor proteins that allow the docking of synaptic vesicle onto the presynaptic terminal, thus initiating the neurotransmitter release process. Yet, the role and fate of synaptotagmins following TBI is unknown. In contrast, proteolysis of axonal proteins such as neurofilament proteins, amyloid precursor protein (APP) and αII-spectrin following TBI has been documented.

SUMMARY OF THE INVENTION

The present invention provides evidence that neuronal protein markers are differentially present in brain tissue after neural injury due to traumatic brain injury as compared with normal subjects. The measurement of these markers, alone or in combination, provides information useful for correlation with extent of injury and a means for assessing recovery as levels of the markers return to normal levels.

Several biomarkers, including CRMP and synaptotagmin, were discovered using a differential proteomics technique. Multidimensional protein separation of naïve and TBI brain samples from a rat model was employed to characterize alteration of the cortical proteome associated with the trauma.

Changes were identified using reverse phase liquid chromatography tandem mass spectrometry and differential abundance was confirmed by correlating semi-quantitative peptide numbers with protein data. The correlation process reduced the number of false-positive differential proteins, refining the list of putative biochemical markers. At least 21 putative biomarkers of TBI that demonstrated a decrease in abundance associated with injury were identified. At least 39 putative markers of TBI were found that showed an increased abundance after TBI.

Two of the proteins with increased abundance after TBI were identified as breakdown products of synaptotagmin and collapsing response mediator protein 2 (CRMP2). The calpain cleavage site for both these proteins was identified and the distinct region of the protein at the cleavage site isolated. The breakdown products for synaptotagmin and CRMP-2 were identified and used as to develop an assay for neural injury.

Cleavage sites for isoforms of CRMP were identified and determined to be useful for detecting traumatic brain injury. CRMP-1, CRMP-3 and CRMP-4 were proteolytically by calpain-3, but not by caspace, after TBI and cleavage products identified. CRMP-5, in contrast to the other CRMP isoforms, did not exhibit calpain degradation products after TBI.

A calpain cleavage site for the neural protein synaptotagmin-1 was identified. The protein decreased after TBI with an accompanying increase in calpain BDP. The cleavage site was identified and used to design a 9-residue peptide to which an antibody was prepared that selectively bound to the BDP but not to intact synaptotagmin.

BRIEF DESCRIPTION OF THE FIGURES

FIG. 5A shows time-dependent changes of CRMP2 proteolysis in rat brain tissue following TBI. Time dependent changes of CRMP2 proteolysis in brain samples from ipsilateral cortex with a 1.6 mm impact TBI 2 hrs to 14 days after injury (2, 6, 24, 48 hr and 3 da, 5 da, 7 da and 14 da). Brain lysates were subjected to immunoblotting and probed with CRMP2, αII spectrin or β-actin antibodies. Quantitative analysis of the intact CRMP2 (62 kDa) and 55 kDa BDP of CRMP2 in ipsilateral cortex were done by densitometry analysis. Values represent means +−S.E.M. n=3. $*p<0.05$ compared with naïve.

FIGS. 5A-5D. FIG. 5B is a densiometric scan of the data shown in FIG. 5A for intact CRMP-2 and the 55 kDa BDP from 2 hr to 14 days post TBI in ipisilateral cortex tissue. Densiometric units are arbitrary, assigning a base number of 20 units based on naïve tissue.

FIG. 5C shows time-dependent changes of CRMP2 proteolysis in rat brain tissue following TBI. Time dependent changes of CRMP2 proteolysis in brain samples from ipsilateral hippocampus with a 1.6 mm impact TBI 2 hrs to 14 days after injury (2, 6, 24, 48 hr and 3 da, 5 da, 7 da and 14 da). Brain lysates were subjected to immunoblotting and probed with CRMP2, αII spectrin or β-actin antibodies. Quantitative analysis of the intact CRMP2 (62 kDa) and 55 kDa BDP of CRMP2 in ipsilateral hippocampus (D) were done by densitometry analysis. Values represent means +−S.E.M. n=3. $*p<0.05$ compared with naïve.

FIG. 5D is a densiometric scan of the data shown in FIG. 5C for intact CRMP-2 and the 55 kDa BDP from 2 hr to 14 days post TBI in ipisilateral cortex tissue. Densiometric units are arbitrary, assigning a base number of 20 units based on naïve tissue.

FIG. 6A shows tissue specificity of CRMP2 as shown on a human tissue panel screen. 20 µg of homogenized human organ specific tissue was separated on a SDS-PAGE gel. CRMP2 specific antibody was used to screen the blot. The protein is very specific for brain tissue and has only slight cross reactivity with lung tissue. This indicates that the SW ELISA, using this antibody would be very brain specific. This blot was probed using mouse anti-CRMP2 (IBL Cat# 11096).

FIG. 6B is a Western blot analysis of human control and TBI CSF collected at different time points showing CRMP2 analysis. CRMP2 has a molecular weight of 65 kDa. The full-length protein is seen with the brain lysate at 62 kDa. The BDP is also seen at 55 kDa. Bands are seen with the TBI CSF from enrollment of the patient (E) to 120 hrs. Control CSF shows only low level of intact protein. BDP is detected at large amounts 12 h post injury. CSF control, Enrollment of patient (E), 12 h, 24 h, 48 h, 72, 120 h post injury. This blot was probed using mouse anti-CRMP2 (IBL Cat# 11096).

FIG. 14 represents the time course of TBI-associated synaptotagmin-1 proteolysis in rat cortex and hippocampus. FIG. 14A is a Western blotting analysis of Syt1 in rat cortex and hippocampus (FIG. 14C) at the indicated time points after TBI, compared to naïve control (N). Beta-actin blots were also performed as protein loading controls. The density of intact Syt1 65 kDa (solid squares for cortex, rhomboid for hippocampus) isoform and BDP-33k (solid round for cortex, empty triangle for hippocampus) in naïve and ipsilateral TBI cortex (FIG. 14B) and hippocampus (FIG. 14D) were plotted against various time points. The results revealed that Syt1 65 kDa decreased significantly, but BDP-33 was significantly increase at the different time point in both cortex and hippocampus after TBI (* $p<0.05$; ** $p<0.01$, n=5).

FIG. 15A is a Western blot showing the increase in the 33 kDa BDP of synaptotagmin in rat hippocampus from 2 hr up 14 days post TBI. For comparison, the level of b-actin in cortex is shown.

FIG. 15B is a densiometric scan of the blots in FIG. 14 A setting level of synaptotagmin at an arbitrary value of 110 and the 33 kDa BDP at 15 based on control levels.

DETAILED DESCRIPTION OF THE INVENTION

Figure 1:
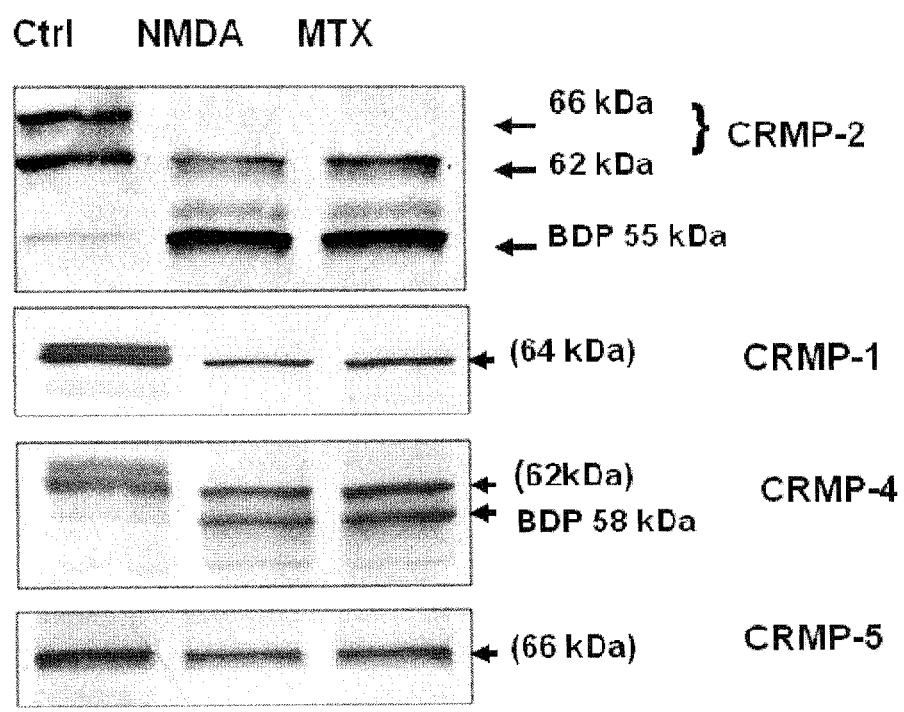
FIG. 1 Primary cortical neurons were exposed to NMDA (200 µM) for 6 hours or maitotoxin (3 nM) for 3 hours. Total protein extracts were separated by SDS-PAGE and immunoblotted with anti-CRMP antibodies. A marked reduction of intact CRMP-2, 1, and 4 was noticed along with the appearance of breakdown products following NMDA and MTX treatment. The same samples were probed with CRMP1, CRMP4 and CRMP5 antibodies. Decrease of CRMP1 and CRMP4 with a 58 kDa and 62 kDa doublet was observed following NMDA and MTX treatment; however, no remarkable change in CRMP5 was detected. Results shown are representatives of three experiments.

The present invention demonstrates that increases in neural protein breakdown products of some members of the CRMP family of neuroproteins are accompanied by a decrease in the intact protein and are associated with traumatic brain injury. The decrease in intact CRMP proteins is due to breakdown products (BDPs) from calpain proteolytic cleavage of CRMP1, CRMP2, and CRMP4.

The invention further demonstrates that increased levels of synaptotagmin breakdown products and decreased levels of intact synaptotagmin-1 protein after exposure to oncotic, apoptotic and excitotoxic conditions and after controlled cortical impact (TBI) in an in vivo model can be detected and related to TBI.

In conjunction with identifying changes in protein expression associated with traumatic brain injury, a neuroproteomics analysis method was used to identify 90 differentially expressed proteins of which 35 were down-regulated and 53 upregulated after traumatic brain injury in an animal model. Of these, the CRMPs and synaptotagmin were tested for use in analysis and diagnostic of TBI.

Cationic Anionic Exchange Liquid Chromatography-1 Dimensional Polyacrylamide Gel Electrophoresis (CAX-PAGE) separation technique was utilized in identifying neural proteins affected by traumatic brain injury in a rat model. In brief, CAX-PAGE is a differential multi-dimension proteomic technique, which can be used for neuroproteomics analysis as an alternative to the conventional 2D Gel Electrophoresis. Differential bands were excised and subsequent protein identification was performed by in-gel digestion followed by reverse phase capillary separation online with LCQ Tandem Mass Spectrometry. Results were analyzed to produce a concise list of 90 differential protein expressions: 35 down-regulated see Table 1, and 53 up-regulated in TBI, see Table 2. Some of the differential down-regulated proteins identified in TBI included cofilin, profilin, CRMP-2, αII-spectrin, GAPDH, MAP2A/B, and hexokinase. C-reactive protein and transferrin along with other breakdown products (MAP1A, CRMP-2, synaptotagmin and αII-spectrin) were elevated in TBI in accordance. These differential proteomic data were further validated by western blot analysis of TBI vs. naïve pooled cortical samples.

Table 1 is a list of proteins with decreased abundance post-TBI.

TABLE 1

Proteins with decreased abundance post-TBI

| Band | Gel MW kDa | Intact MW kDa | Protein Accession # | Protein Name | # pep in Naïve | # pep in TBI | % Cov. |
|---|---|---|---|---|---|---|---|
| 6A | 56 | 72.1 | XP_237959 | Annexin A11 | 6 | 0 | 11.0% |
|  |  | 57.2 | XP_214535 | Aldehyde Dehydrogenase Family 7 | 3 | 1 | 7.4% |

TABLE 1-continued

Proteins with decreased abundance post-TBI

| Band | Gel MW kDa | Intact MW kDa | Protein Accession # | Protein Name | # pep in Naïve | # pep in TBI | % Cov. |
|---|---|---|---|---|---|---|---|
| 6B | 20 | 18.5 | AAH86533 | Cofilin 1 | 5 | 3 | 28.3% |
| 8A | 15 | 14.9 | NP_071956 | Profilin 1 | 2 | 0 | 22.2% |
| 9B | 56 | 57.8 | AAB93667 | M2 pyruvate kinase | 15 | 12 | 29.8% |
| 9C | 55 | 50.9 | XP_227366 | Alpha enolase (non-neural enolase) | 2 | 0 | 7.05% |
| | | 57.8 | AAB93667 | M2 pyruvate kinase | 7 | 2 | 15.40% |
| 9D | 50 | 47.1 | AAH78896 | Enolse1 protein | 5 | 3 | 19.30% |
| 9E | 34 | 35.8 | XP_573896 | Glyceraldehyde-3-phosphate dehydrogenase | 5 | 1 | 23.0% |
| 10A | 105 | 102.4 | NP_036866 | Hexokinase 1 | 4 | 0 | 5.5% |
| 10B | 85 | 85.4 | NP_077374 | Aconitase 2. mitochondrial | 7 | 1 | 11.2% |
| 10C | 72 | 74.8 | XP_215897 | Acetyl-CoA synthetase 2 | 3 | 0 | 10.4% |
| 10D | 21 | 22.4 | AAL66341 | Neuronal protein 22 | 3 | 0 | 18.6% |
| 12A | 45 | 44.8 | AAH83568 | Phosphoglycerate kinase 2 | 4 | 0 | 10.8% |
| | | 44.5 | NP445743 | Phosphoglycerate kinase 1 | 5 | 0 | 13.2% |
| 13A | 70 | 70.4 | CAA49670 | Hsc70-ps1 | 11 | 5 | 22.6% |
| 13B | 58 | 61.3 | NP_036702 | Glutamate dehydrogenase 1 | 4 | 0 | 8.6% |
| 13C | 37 | 39.3 | NP_036627 | Aldolase A | 3 | 0 | 9.3% |
| | | 39.2 | NP_036629 | Aldolase C. fructose-biphosphate | 4 | 0 | 16.5% |
| 13D | 34 | 31.1 | NP_071633 | Dimethylarginine dimethylaminohydrolase 1 | 3 | 1 | 10.5% |
| 17A | 64 | 62.2 | NP_071633 | Collapsin response mediator protein 2 | 7 | 4 | 15.9% |
| 23A | 200 | 182.2 | NP_037198 | Microtubule-associated protein 2 | 5 | 1 | 3.4% |

MW = molecular weight;
pep = number of peptides;
% Cov. = % of sequence coverage Table 2 is a list of proteins found to increase in abundance after TBI.

TABLE 2

Proteins with increased abundance post-TBI

| Band | Gel MW kDa | Intact MW kDa | Protein Accession # | Protein Name | # pep in Naïve | # pep in TBI | % Cov. |
|---|---|---|---|---|---|---|---|
| 1A | 31 | 29.6 | XP_226922 | Carbonic anhydrase | 3 | 6 | 30.0% |
| 6B | 20 | 20.6 | NP_543180 | ADP-Ribosylation Factor 3 | 1 | 3 | 17.7% |
| 7A | 75 | 75.8 | NP_058751 | Transferrin | 0 | 8 | 13.2% |
| | | 76.7 | AAP97736 | Liver regeneration-related protein | 0 | 4 | 5.5% |
| 8A | 15 | 15.2 | XP_340780 | Hemoglobin alpha chain | 0 | 5 | 33.8% |
| | | 15.9 | NP_150237 | Hemoglobin beta chain | 0 | 2 | 15.0% |
| 9A | 77 | 76.7 | AAP97736 | Liver regeneration-related protein | 0 | 2 | 2.6% |
| 9B | 56 | 41.5 | NP_445800 | Fetuin beta | 0 | 4 | 11.6% |
| | | 55.9 | XP_227088 | 3-Oxoacid CoaTransferase | 1 | 4 | 10.4% |
| 9E | 34 | 36.4 | NP_150238 | Malate dehydrogenase 1. NAD (soluble) | 0 | 2 | 5.7% |
| | | 36.6 | NP_036727 | Lactate dehydrogenase B | 1 | 4 | 13.8% |
| | | 35.6 | AAH63165 | Malate dehydrogenase. mitochondrial | 0 | 2 | 7.6% |
| 10C | 72 | 75.8 | NP_058751 | Transferrin | 0 | 3 | 13.2% |
| 13A | | 60.1 | JX0054 | Carboxylesterase E1 precursor | 0 | 5 | 13.6% |
| 13B | 58 | 46.1 | NP_071964 | Serine protease inhibitor alpha 1 | 0 | 8 | 15.8% |
| 13D | 34 | 38.5 | NP_036714 | Haptoglobin | 0 | 4 | 11.8% |
| 13E | 22 | 24.8 | JX0222 | Ubiquitin carboxy-terminal hydrolase L1 | 1 | 3 | 13.9% |

TABLE 2-continued

Proteins with increased abundance post-TBI

| Band | Gel MW kDa | Intact MW kDa | Protein Accession # | Protein Name | # pep in Naïve | # pep in TBI | % Cov. |
|---|---|---|---|---|---|---|---|
| 14A | 50 | 46.1 | NP_071964 | Serine protease inhibitor alpha 1 | 0 | 8 | 14.8% |
| 17A | 64 | 68.2 | NP_872280 | Serine protease inhibitor 2a | 0 | 7 | 10.0% |
|  |  | 47.7 | AAA41489 | T-kininogen.alpha-1 major acute phase protein | 0 | 4 | 9.5% |
|  |  | 68.7 | AAH85359 | Albumin | 8 | 11 | 23.0% |
|  |  | 47.7 | NP_001009628 | Alpha-1 major acute phase protein prepeptide | 0 | 2 | 5.8% |
| 18A | 160 | 165.2 | NP_075591 | Murinoglobulin 1 homolog | 0 | 5 | 4.5% |
| 18B | 54 | 53.5 | NP_036696 | Group specific component protein | 0 | 7 | 11.6% |
|  |  | 50.5 | P50398 | Guanosine diphosphate dissociation inhibitor 1 | 1 | 4 | 17.6% |
|  |  | 62.2 | NP_071633 | Collapsin response mediator protein 2 *(BDP) | 0 | 3 | 5.9% |
| 19A | 160 | 165.2 | NP_075591 | Murinoglobulin 1 homolog | 4 | 9 | 7.9% |
|  |  | 163.7 | XP_216246 | Similar to alpha-1-inhibitor III precursor | 3 | 7 | 5.5% |
| 20A | 120 | 120.6 | A35210 | Ferroxidase | 0 | 15 | 14.5% |
|  |  | 122.2 | AAA40917 | Ceruloplasmin | 0 | 9 | 6.6% |
|  |  | 271.6 | P16086 | Spectrin alpha chain. brain *(BDP) | 0 | 4 | 1.9% |
| 20B | 25 | 25.5 | NP_058792 | C-reactive protein | 0 | 2 | 8.7% |
|  |  | 42.6 | AAH87656 | Brain creatine kinase *(BDP) | 1 | 3 | 13.6% |
|  |  | 27.8 | NP_001008218 | Proteasome subunit. alpha type 7 | 0 | 4 | 19.7% |
|  |  | 27.7 | BAA04534 | 14-3-3 protein zeta-subtype | 2 | 5 | 22.4% |
|  |  | 27.7 | BAA04533 | 14-3-3 protein theta-subtype | 1 | 3 | 13.9% |
|  |  | 28.2 | BAA04259 | 14-3-3 protein eta-subtype | 0 | 3 | 13.8% |
|  |  | 28.3 | BAA04261 | 14-3-3 protein gamma-subtype | 0 | 2 | 8.1% |
| 29A | 37 | 47.4 | XP_343206 | Synaptotagmin *(BDP) | 0 | 4 | 10.7% |

MW = molecular weight;
pep = number of peptides;
% Cov. = % of sequence coverage
*(BDP) denotes a suspected breakdown product Cationic Anionic Exchange Liquid Chromatography-1 Dimensional Polyacrylamide Gel Electrophoresis (CAX-PAGE) separation technique was utilized in identifying neural proteins affected by traumatic brain injury in a rat model. In brief, CAX-PAGE is a differential multi-dimension proteomic technique, which can be used for neuroproteomics analysis as an alternative to the conventional 2D Gel Electrophoresis. Differential bands were excised and subsequent protein identification was performed by in-gel digestion followed by reverse phase capillary separation online with LCQ Tandem Mass Spectrometry. Results were analyzed to produce a concise list of 90 differential protein expressions: 35 downregulated and 53 upregulated in TBI. Some of the differential downregulated proteins identified in TBI included cofilin, profilin, CRMP-2, αII-spectrin, GAPDH, MAP2A/B, and hexokinase. Also, C-reactive protein and transferrin along with other breakdown products (MAP1A, CRMP-2, synaptotagmin and αII-spectrin) were elevated in TBI in accordance. These differential proteomic data were further validated by western blot analysis of TBI vs. naïve pooled cortical samples.

Collapsin response mediator proteins (CRMPs) are a family of cytosolic proteins that are highly expressed in the brain. They are involved in different aspects of axonal outgrowth, neuronal morphogenesis and cell death. CRMP1, 2 and 5 play an essential role in growth cone collapse in response to repelling guidance cues, such as semaphorin 3A or lysophosphatidic acid. CMRP4 is highly expressed in post-mitotic neurons in the early embryonic brain and is identified to involve in the brain development. CRMP4 is also found in regions that retain the capability of neurogenesis or display axonal outgrowth and/or synaptic rearrangement during adulthood.

CRMP2 was the first CRMP discovered, and is concentrated in growing axons, dendrites, and the cytoplasm of differentiating neurons. CRMP2 is important in the determination of neuronal polarity and axonal elongation. Highly phosphorylated CRMP2 may play a role in neurodegeneration, as observed in neurofibrillary tangles in Alzheimer's diseased brains. A growing body of evidence suggests that CRMP2 may also participate in the pathophysiology of other neurological disorders. Decreased expression of CRMP2 has been reported in fetal brains with Down's syndrome, patients with mesial temporal lobe epilepsy, focal ischemic rat brain and in the frontal cortex of patients suffering from psychiatric disorders (schizophrenia, bipolar, or major depression disorders).

An increase in CRMP2 has been observed after chronic anti-depressant treatment in rat hippocampus. CRMP2 has also been reported to mediate axonal damage and neuronal death via a semaphorine-CRMP pathway. The pathophysiology of neuronal injury appears to vary among neurological disorders but there is some indication that CRMP2 may be involved. CRMP3 also has a role in neural function. In vitro calpain-cleaved CRMP-3 translocates into the nucleus to evoke neuronal death in response to excitotoxicity.

There has been no indication of the involvement, if any, of CRMP family members other than CRMP2, nor is there any known association with neural cell injury. In fact, because sequence homology among the CRMP family members is only 50-75%, there was no reason to expect that several of the CRMP variants would undergo proteolysis similar to CRMP2.

The integrity of CRMPs (CRMP1, 2, 4, 5) after in vitro neurotoxin treatment (FIG. 1) and in vivo traumatic brain injury (TBI) was investigated. In maitotoxin (MTX) or NMDA treatment in primary cortical neurons, a dramatic decrease of intact CRMP1, 2 and 4 proteins was observed, accompanied by the appearance of a distinct 55 kDa (CRMP2) or 58 kDa (CRMP4) breakdown product (BDP), respectively. Calpain inhibition prevented NMDA-induced CRMP2 proteolysis and redistribution of CRMP2 from neurites to cell body, while attenuating neurite damage and neuronal cell injury.

Similarly, CRMP1, 2 (see FIG. 2) and 4 were also found degraded in rat cortex and hippocampus following controlled cortical impact (CCI) in vivo, a model of TBI. The appearance of the 55 kDa CRMP2 BDP was observed in a time-dependent manner with a significant increase between 24 and 48 hours in the ipsilateral cortex, and at 48 hours in the hippocampus (see FIGS. 5A-5D). The 55 kDa CRMP2 BDP appearance following TBI was reproduced by in vitro incubation of naïve brain lysate with calpain, but not caspase-3. Sequence analysis revealed several possible cleavage sites near the C-terminus of CRMP2.

These results demonstrated that CRMP1, 2 and 4 are degraded following acute traumatic or neurotoxic injury. Furthermore, calpain was shown to mediate proteolysis of CRMP2 following excitotoxic injury and TBI, which appears to correlate with neuronal cell injury and neurite damage. Calpain-mediated truncation of CRMPs following TBI may have effects on further inhibiting post-injury neurite regeneration.

Synaptotagmin was also shown to be a good biomarker for TBI in that there was a distinct decrease in synaptotagmin-1 levels after TBI, accompanied by an increase in associated BDPs. The 65 kDa synaptotagmin-1 protein was fragmented by calpain into N-terminal fragments (33-36 kDa) in rat cerebrocortical cultures under oncotic (maitotoxin), apoptotic (staurosporine) and excitotoxic challenge (NMDA) and in rat cortex and hippocampus between 2 hours and 3 days after controlled cortical impact (a rat model of TBI).

Using N-terminal microsequencing, the synaptotagmin-1 cleavage site was identified as between Gly-111 and Lys-112, thereby dissociating the transmembrane N-terminal domain from the cytosolic calcium-binding C2 domain.

Through the use of total synaptotagmin and fragment-specific antibodies, extensive disorganization of synaptotagmin-coupled vesicles and movement away from the presynaptic terminal was observed in Maitotoxin and NMDA-treated cerebrocortical neurons and cerebellar granule neurons.

Taken together, the data indicated that calpain-mediated synaptotagmin fragmentation is involved in synaptic dysfunction and abnormality of neurotransmission.

EXAMPLES

The following examples are provided as illustrations of the invention and are in no way to be considered limiting. Additional details are found in the description of the figures to which reference is made.

Materials and Methods

Primary Cortical Neuron Culture

Primary cortical neurons from first post-natal day Sprague-Dawley rat brains were plated on poly-L-lysine coated culture plates (Erie Scientific, Portsmouth, N.H., U.S.A.). Cells were dissociated with trypsin and DNase I, re-suspended in 10% plasma-derived horse serum (PDHS) in Dulbecco's modified Eagle's medium (DMEM), and plated on poly-L-lysine treated 35 mm (density: $3.0 \times 10^6$ cells per well) plates. Cells were allowed to grow in an atmosphere of 10% $CO_2$ at 37° C. for three days and then treated with 1 μM 4-amino-6-hydrazino-7-β-D-ribofuranosyl-7H-pyrrolo (2,3-d)-pyrimidine-5-carboxamide (ARC) for two days. The ARC was removed and fresh 10% PDHS was added in DMEM, after which the cells were grown for an additional 10-14 days.

Rat Primary Cerebrocortical Culture

Cerebrocortical cells harvested from 1-day old Sprague-Dawley rat brains were plated on poly-L-lysine coated on 6-well culture plates (Erie Scientific, Portsmouth, N.H., USA) at a density of $4.36 \times 10^5$ cells/mL. Cultures were maintained in Dulbecco's modified Eagle's medium (DMEM) with 10% fetal bovine serum in a humidified incubator in an atmosphere of 10% $CO_2$ at 37° C. After 5 days in culture, the media were changed to DMEM with 5% horse serum. Subsequent media changes were performed three times a week. Experiments were performed on days 10 to 11 in vitro when astroglia had formed a confluent monolayer beneath morphologically mature neurons.

Cerebrocortical cultures (12-day-old) from above were washed three times with serum-free MEM. The cultures then were either untreated (control) or challenged with 0.1 mM maitotoxin (MTX) alone for 3 hours, or to 5 Mm EDTA and 300 μM N-Methyl-D-Asparate (NMDA) for 24 hours as described previously (12-14), respectively.

In addition to untreated controls, the following conditions were used: maitotoxin (MTX) (3 nM; WAKO Chemical USA Inc., Richmond, Va.) as a calpain-dominated challenge for three hours; apoptotic inducer staurosporine (STS) (0.5 μM; Sigma, St. Louis, Mo.) for 24 hours; the $Ca^{2+}$ chelator ethylene diamine tetra-acetic acid (EDTA) (5 mM; Sigma) for 24 hours as a caspase-dominated challenge; and NMDA (200 μM; Sigma) for 3 to 24 hours as an excitotoxic challenge.

Cell Lysates and Tissue Preparation

A ceramic pestle bow was placed on dry ice and cooled for 3 min. The tissue was weighed and placed into the chilled ceramic pestle on the dry ice until frozen and hard. Fresh tissue should be cut into small pieces on dry ice, then ground as fine as possible to look like powder. The powdered tissue is transferred to a 1.5 ml centrifuge tube and 1× Triton extraction buffer (1 g tissue homogenate/2-3 ml buffer, add DTT and protease inhibitor cocktails fresh) added to the centrifuge tube. Homogenization is carried out for 30-60 strokes. The homogenized material is allowed to stand on ice for 30 min, vortexed for 10 strokes, and placed on ice again for 30 min.

The procedure is repeated this 2 times before a final spin at 4° C., max speed (14,000 rpm) for 30 min. The supernatant is removed and protein concentration determined with DC protein assay. Triton extraction buffer: Tris, pH 7.4 (20 µl), NaCl (150 mM), EDTA (5 µl), EGTA (5 mM), TritonX-100 (1%), dH₂O (180 ml), Protease inhibitor 1× from 10× stock (Roche), DTT (1 mM, fresh).

Immunocytochemistry

Figure 7:
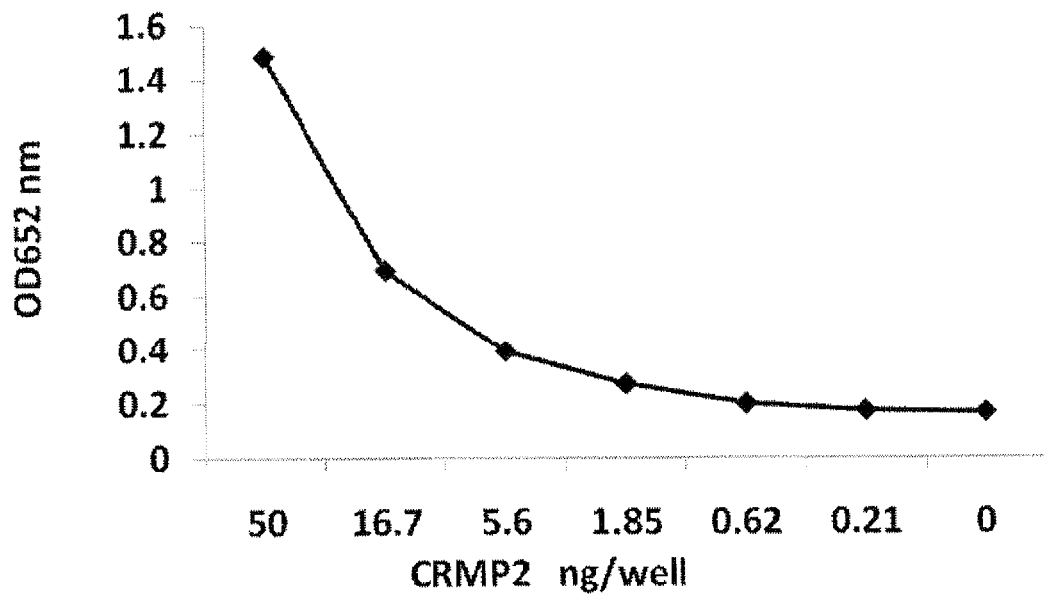
FIG. 7 is a CRMP2 SW Elisa standard curve measured at 652 nm for GST-CRMP2 recombinant protein (Kinasource, cat# SU-040) detected with rabbit Pab (Santa Cruz, Cat#sc-30228) assay employing 1 µg/ml. The second anti-rabbit IgG-HRP was Amersham (cat#NA934V, 1:1000).

GST-CRMP2 recombinant protein was purchased from Kinasource (cat#SU-040), capture antibody, Mab from IBL (cat# 11098) and detection Ab from Santa cruz, cat# sc-30228, $2^{nd}$ anti-rabbit IgG-HRP from Amershamm cat# NA934V. A CRMP2 SW ELISA standard curve is shown in FIG. 7.

Figure 8:
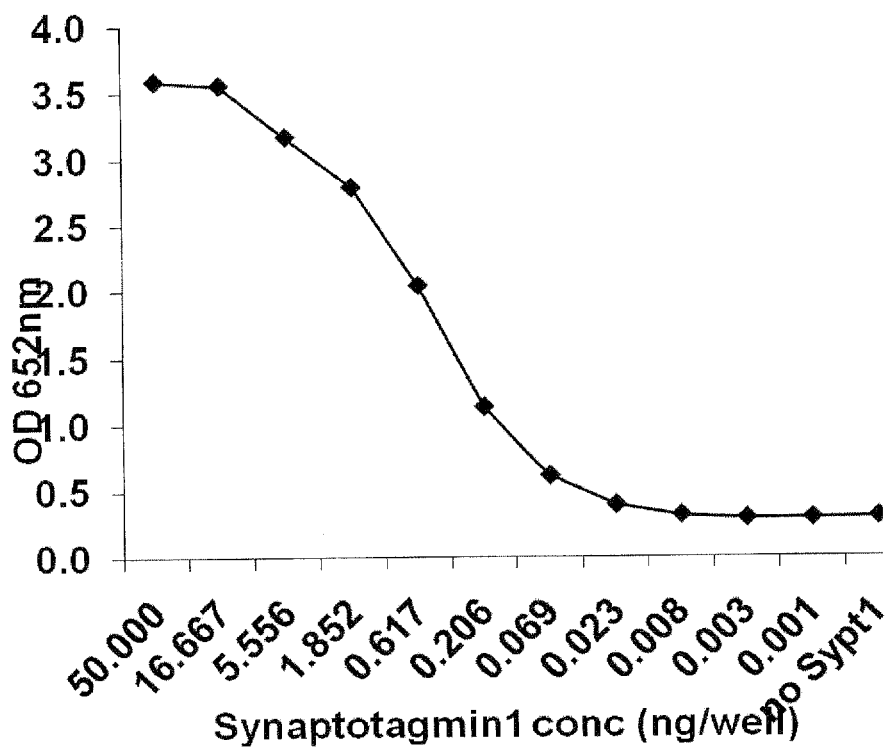
FIG. 8 is a synaptotagmin1 standard curve by SW ELISA.

A typical SW ELISA standard curve for synaptotagmin1 is shown in FIG. 8.

Rat TBI Model

A controlled cortical impact (CCI) device was used to model TBI. Adult male (280-300 g) Sprague-Dawley rats (Harlan: Indianapolis, Ind.) were anesthetized with 4% isoflurane in a carrier gas of oxygen (4 min.) followed by maintenance anesthesia of 2.5% isoflurane in the same carrier gas. Core body temperature was monitored continuously by a rectal thermistor probe, and was maintained at 37±1° C. by placing an adjustable temperature controlled heating pad beneath the rats. Animals were mounted in a stereotactic frame in a prone position and secured by ear and incisor bars. A midline cranial incision was made, the soft tissues reflected, and a unilateral (ipsilateral) craniotomy (7 mm diameter) was performed adjacent to the central suture, midway between bregma and lambda. The dura mater was kept intact over the cortex. Brain trauma was produced by impacting the right cortex (ipsilateral cortex) with a 5 mm diameter aluminum impactor tip (housed in a pneumatic cylinder) at a velocity of 3.5 m/s with a 1.6 mm compression and 150 ms dwell time (compression duration).

These injuries were associated with different magnitudes of local cortical contusion and more diffuse axonal damage. Velocity was controlled by adjusting the pressure (compressed $N_2$) supplied to the pneumatic cylinder. Velocity and dwell time were measured by a linear velocity displacement transducer (LUCAS SHAEVITZ model 500 HR; Detroit, Mich.) that produced an analogue signal that was recorded by a storage-trace oscilloscope (BK Precision, model 2522B; Placentia, Calif.).

Sham-injured control animals underwent identical surgical procedures but did not receive an impact injury. Appropriate pre- and post-injury management was maintained to insure compliance with appropriate guidelines.

Collection of Brain Tissue

At the 8 post-CCI time points (2, 6, 24 hours and 2, 3, 5, 7, 14 days), animals were anesthetized and killed by decapitation. Brains were immediately removed, rinsed with ice cold PBS and halved. Two different brain regions (cortex and hippocampus) were removed from the right and left hemispheres, rinsed in ice cold PBS, snap-frozen in liquid nitrogen, and stored at −80° C. until use. For immunohistochemistry, brains were quick frozen in dry ice slurry, then sectioned via cryostat (20 µm) onto SuperFrost Plus Gold® (Fisher Scientific) slides and frozen at −80° C. until used. The same tissue as was collected for the left as collected for the right side. For Western blot analysis, the brain samples were pulverized to a fine powder with a small mortar and pestle set over dry ice. The pulverized brain tissue was then lysed for 90 minutes at 4° C. with lysis buffer containing 50 mM Tris-HCl (pH 7.4), 5 mM EDTA, 5 mM EDTA, 1% Triton X-100, and 1 mM DTT (added fresh), 1× protease inhibitor cocktail (Riche Biochemicals). Brain cortex lysates were then centrifuged at 100,000 g for 10 minutes at 4° C. The supernatant was retained, and a DC protein assay (Bio-Rad, Hercules, Calif.) was performed to determine protein concentration. Naïve cortex lysate was prepared in the same manner. Samples were snap-frozen and stored at −85° C. until used.

In Vitro Calpain-2 and Caspase-3 Digestion

In vitro digestion of rat brain lysate (5 mg) was performed with the purified proteases human erythrocyte calpain-1, rat recombinant calpain-2 (Calbiochem, San Diego, Calif.) and recombinant human caspase-3 (Chemicon, Temecula, Calif.) in a buffer containing 100 mM Tris-HCl (pH 7.4) and 20 mM DTT. For calpain, 2 mM $CaCl_2$ was also added, and then incubated at room temperature for 30 minutes. For caspase-3, samples were incubated at 37° C. for four hours. Protease reactions were stopped by the addition of calpain inhibitor SJA6017 to a concentration of 30 µM (Senju Pharmaceuticals, Kobe, Japan) or pan-caspase inhibitor Z-VAD to a concentration of 20 µM and a protease inhibitor cocktail solution.

SDS-PAGE, Electrotransfer and Immunoblot Analysis

Protein concentrations of cell or tissue lysates were determined via Bio-Rad DC Protein Assay (Bio-Rad, Hercules, Calif.). Protein balanced samples were prepared for sodium dodecyl sulfate-polyacrylamide gel electrophoresis (SDS-PAGE) in a two-fold loading buffer containing 0.25 M Tris (pH 6.8), 0.2 M DTT, 8% SDS, 0.02% bromophenol blue, and 20% glycerol in distilled water. Samples were heated for 90 seconds at 90° C. and centrifuged for 2 minutes. Twenty micrograms (20 µg) of protein per lane were routinely resolved by SDS-PAGE on Tris-glycine gels for 2 hours at 130V. Following electrophoresis, separated proteins were laterally transferred to polyvinylidene fluoride (PVDF) membranes in a transfer buffer containing 39 mM glycine and 48 mM Tris-HCl (pH 8.3) 5% methanol at a constant voltage of 20V for 2 hours at ambient temperature in a semi-dry transfer unit (Bio-Rad) by the semi-dry method.

Rat CRMP5 antibody (targeting to residues 369-564, Chemicon, Temecula, Calif.) was dialyzed with PBS using Slide-A-Lyzer MINI Dialysis Units, (Pierce, 3.5MWCO, 69550, Rockford, Ill.). Then CRMP5 was biotinylated by using EZ-link, sulfo-NHS-LC-LC-biotin by following the manufacture's instructions. Membranes were blotted either with anti-CRMP-1, or -4 (targeting residues 499-511, Chemicon), biotinylated-anti-CRMP5 antibodies or anti-CRMP2 (C4G) or a C-terminal anti-CRMP2 antibody raised against a synthetic peptides of residues 551-559), and developed with biotin and avidin-conjugated alkaline phosphatase (this step was skipped in CRMP5 blotting) and nitroblue tetrazolium and 5-bromo-4-chloro-3-indolyl phosphate. Quantitative evaluation of protein levels was performed via computer-assisted densitometric scanning (NIH Image J V.1.6 software).

After electrotransfer, blotting membranes were blocked for 1 hour at ambient temperature in 5% non-fat milk in TBS and 0.05% Tween-2 (TBST), then incubated in primary monoclonal synaptotagmin-1 antibody (BD Cat# 610434) in TBST with 5% milk at 1/50 dilution as recommended by the manufacturer at 4° C. overnight, followed by three washes with TBST and a 2 hour incubation at ambient temperature with a secondary antibody linked to biotinylated secondary antibody (Amersham, Cat # RPN1177v1) followed by a 30 min incubation with strepavidin-conjugated alkaline phosphatase (calorimetric method). Colorimetric development was performed with a one-step BCIP NBT reagent (KPL, Cat # 50-81-08). Molecular weights of intact synaptotagmin-1 protein and their potential breakdown products (BDPs) were assessed by running along side rainbow colored molecular weight standards (Amersham, Cat # RPN800V).

Semi-quantitative evaluation of intact synaptotagmin-1 protein and BDP level was performed via computer-assisted densitometric scanning (Epson XL3500 high resolution flatbed scanner) and image analysis with Image J software (NIH). Even loading of samples onto different lands may occur despite careful protein concentration determination and careful sample handling and gel loading (20 mg per land). To overcome this source of variability, beta-actin (polyclonal, Sigma, #A5441) blots were performed routinely as protein loading evenness control. BDP fragment-specific antibody was raised in rabbit, using the unique peptide sequence (KT-MKDQALK, SEQ D NO:3) (based on a novel cleavage site). Synthetic peptides were made and coupled to carrier protein Keyhole Limpet Hemocyanin (KLH) before injecting into the rabbit for polyclonal antibody production.

In Vitro Protease Digestion of Synaptotagmin-1

Brain tissue collection and preparation were as described, but without the use of the protease inhibitor cocktail (see above). In vitro protease digestion of naïve rat hippocampus lysate (5 mg) with purified proteases at different concentration: substrate protein and ratio: human calpain-2 (Calbiochem, Cat# 208715 1 µg/µl) and recombinant human caspase-3 (Chemicon Cat# cc119, caspase-3, 1 U/µl) were performed in a buffer containing 100 mM Tris-HCl (pH 7.4) and 20 mM dithiothreitol. For calpain-2, 10 mM $CaCl_2$ was also added, and then incubated at room temperature for 30 minutes. For caspase-3 digestion, 2 mM EDTA was added instead of $CaCl_2$, and was incubated at 37° C. for 2 hours.

Identification of Synaptotagmin-1 Cleavage Site

The synaptotagmin-1 protein which was digested was separated by SDS-PAGE and electrotransfer to PVDF members. The PVDF membrane protein bands were visualized by Coomassie blue staining (80% methanol, 5% acetic acid and 0.05% Coomassie brilliant blue R-250) for 1 minute. The BDP band (based on Western blot results) was cut out and subjected to N-terminal microsequencing to identify its new N-terminal sequence. By matching the sequence generated from BDP band analysis with the full-length protein sequences in the rat proteome database with bioinformatic tools such as MASCOT, the cleavage site of the protein substrate can be identified. Using this method, the MBP BDP cleavage sites in vivo were identified after TBI.

Semi-quantitative evaluation of protein levels on immunoblots was performed via computer-assisted 1-dimensional densitometric scanning (Epson expression 8836XL high-resolution flatbed scanner and NIH Image J densitometry software). Data were acquired in arbitrary densitometric units. Changes in any outcome parameter will be compared to the appropriate control group. Consequently, magnitude of change from control in one model system was directly compared to those from any other model system. 6 replicate data were evaluated by analysis of variance (ANOVA) and post-hoc Tukey tests. A value of $p<0.05$ was taken as significant.

Statistical Analysis

All experiments described were performed at least in triplicate. Densitometric values represent the mean ±S.E.M. Statistical significance was determined using a one-way ANOVA test, with a significance level of $p<0.01$, except where indicated otherwise.

Densitometric quantification of the immunoblot bands was performed using Epson expression 8836XL high-resolution flatbed scanner and NIH image J densiometry software. Data were acquired in arbitrary densiometric units (AU) and transformed to percentages of the densiometric levels obtained from scans of control samples visualized on the same plots.

Changes in the outcome in TBI immunoblot were compared to the appropriate control (naive) group. 4 replicate of naïve and 4 of TBI were evaluated for statistical significance. Statistical analysis was done using Sigmstat software and student's t-test was used to draw comparisons between the western blot intensities in the TBI and the naïve groups. A value of $p \leq 0.05$ was considered to be significant.

Example 1

Proteolysis of CRMP2

The integrity of CRMP2 following NMDA and MTX neurotoxin induction in primary cortical neurons was examined. A marked reduction in the intact CRMP-2 (66 kDa and 62 kDa) was noticed along with the appearance of a 55 kDa band after excitotoxic injury (200 µM NMDA) in rat primary cortical neuron culture (FIG. 1). Similar results were observed after MTX treatment.

Two anti-phsopho-CRMP2 specific antibodies (3F4 and C-terminal Phospho-CRMP-2) were used to rule out the possibility that the 55 kDa band was due to de-phosphorylation. The altered profile of the 66 kDa and 62 kDa CRMP2 was not observed after NMDA and MTX treatment (data not shown). Thus, the 55 kDa fragment was likely a breakdown product of CRMP2.

The integrity of CRMP1, 4 and 5 was then examined under identical conditions. Decreases in intact CRMP1 and CRMP4 were observed, as well as the increase of a 58 kDa CRMP4 band; however, CRMP5 levels remained unchanged following neurotoxic treatment.

CRMP2 dynamics were further examined by following NMDA (200 µM) induction using a time course analysis (FIGS. 5A-5D). The 55 kDa CRMP2 BDP appeared by 3 hours, and became prominent within 24 hours in ipsilateral cortex and hippocampus samples. The densitometric analysis showed that the reduction of intact CRMP2 was paralleled by the increased 55 kDa BDP over time.

Example 2

Inhibition of CRMP2 Proteolysis

The apoptosis inducer staurosporine (STS, 0.5 µM), a calpain and caspase mixed challenge, and the calcium chelator EDTA (5 mM), a caspase-dominant challenge, were used in primary cortical neurons. Results showed that intact 62 kDa CRMP2 was rapidly degraded to the 55 kDa BDP upon STS treatment, but not upon the caspase-activating EDTA treatment. STS-mediated generation of the 55 kDa CRMP2 BDP was also effectively blocked by SJA6017, while Z-VAD offered no protection. The production of the 55 kDa CRMP2 BDP strikingly paralleled the production of the 150 and 145 kDa αII-spectrin breakdown products, which were monitored as markers for calpain activity in NMDA and STS treatment.

Example 3

Blocking of CRMP2 Redistribution

LDH release assays were performed to determine the role of calpain and caspase inhibition on NMDA induced neuronal cell injury, and to draw a link with CRMP2 degradation. The release of LDH, normally present in the cytoplasm of neurons, into the cell culture media can be used as a measure of dying cells. Results showed that NMDA treatment induced CRMP2 proteolysis in a time-dependent manner. NMDA treatment induced significant neuron death after a 3 hour induction, peaking at 24 hours, which is consistent with the producing of the 55 kDa CRMP2 BDP. Moreover, the calpain inhibitor (SJA6017) provides significant protection within 6 hours, while the caspase inhibitor (Z-VAD) has no protection throughout NMDA treatment.

The distribution of CRMP2 following 6 hours' NMDA treatment with or without calpain and caspase inhibitor was examined to further explore the association of CRMP2 and NMDA induced neurite damage. In a normal healthy state, neurons have healthy, long neurites. Under higher magnification, CRMP2 is more prominently observed in neurites than in the cell body (arrow, control, lower panel).

Post-CCI time courses of cortical and hippocampal rat brains were used to assess the temporal dynamics of CRMP2 following TBI. The amount of intact 62 kDa CRMP-2 decreased from 6 hours to 3 days in correspondence with an increase of the 55 kDa BDP. The change was significant for both the intact and the 55 kDa CRMP-2 BDP at 24 and 48 hours in ipsilateral cortex (FIGS. 5A and 5B), while significant changes in the hippocampus were observed between 24 hours and 3 days (FIGS. 5C and 5D). The level of intact and cleaved CRMP-2 returns to control by day 5 after TBI in cortex and hippocampus as shown by western blot.

Figures 5A, 5B:
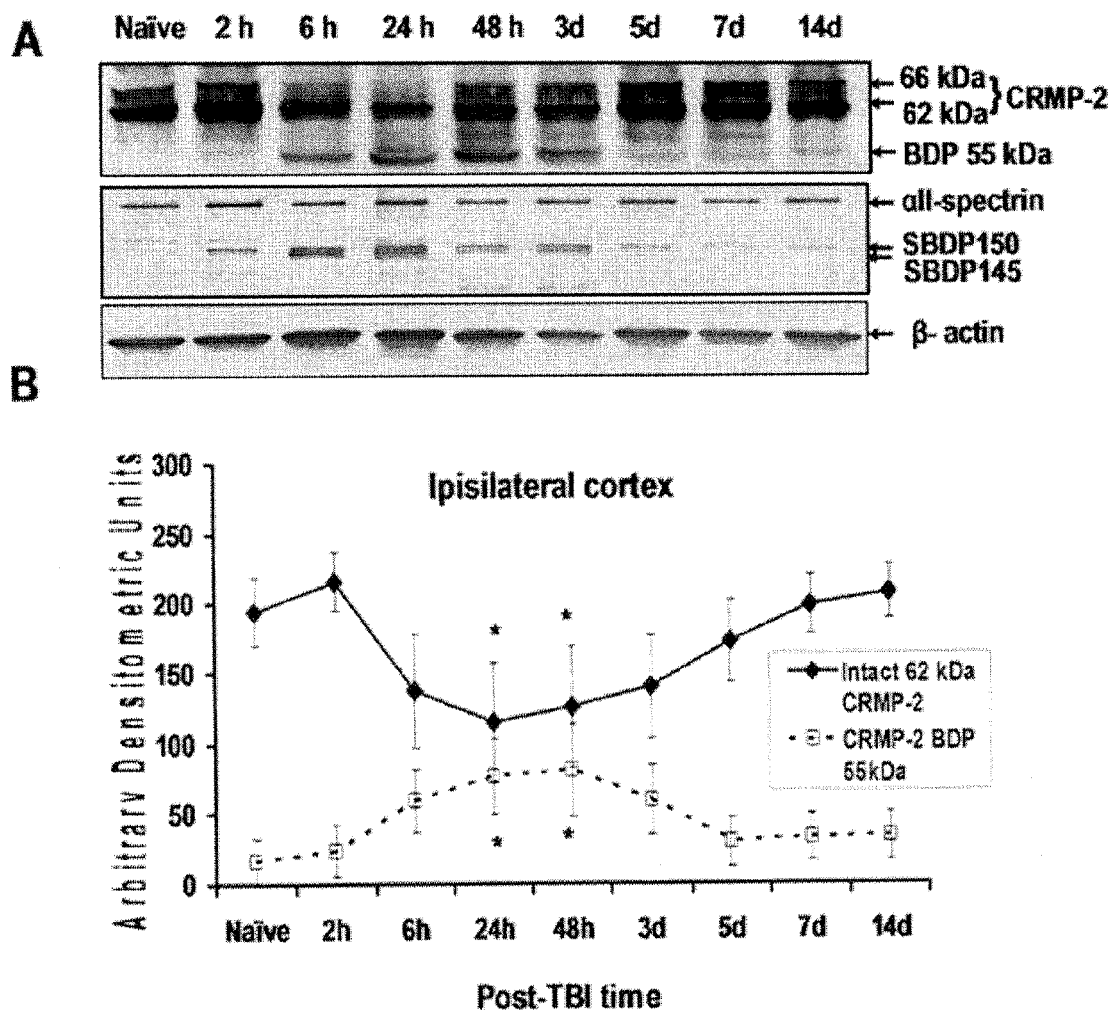
Figures 5C, 5D:
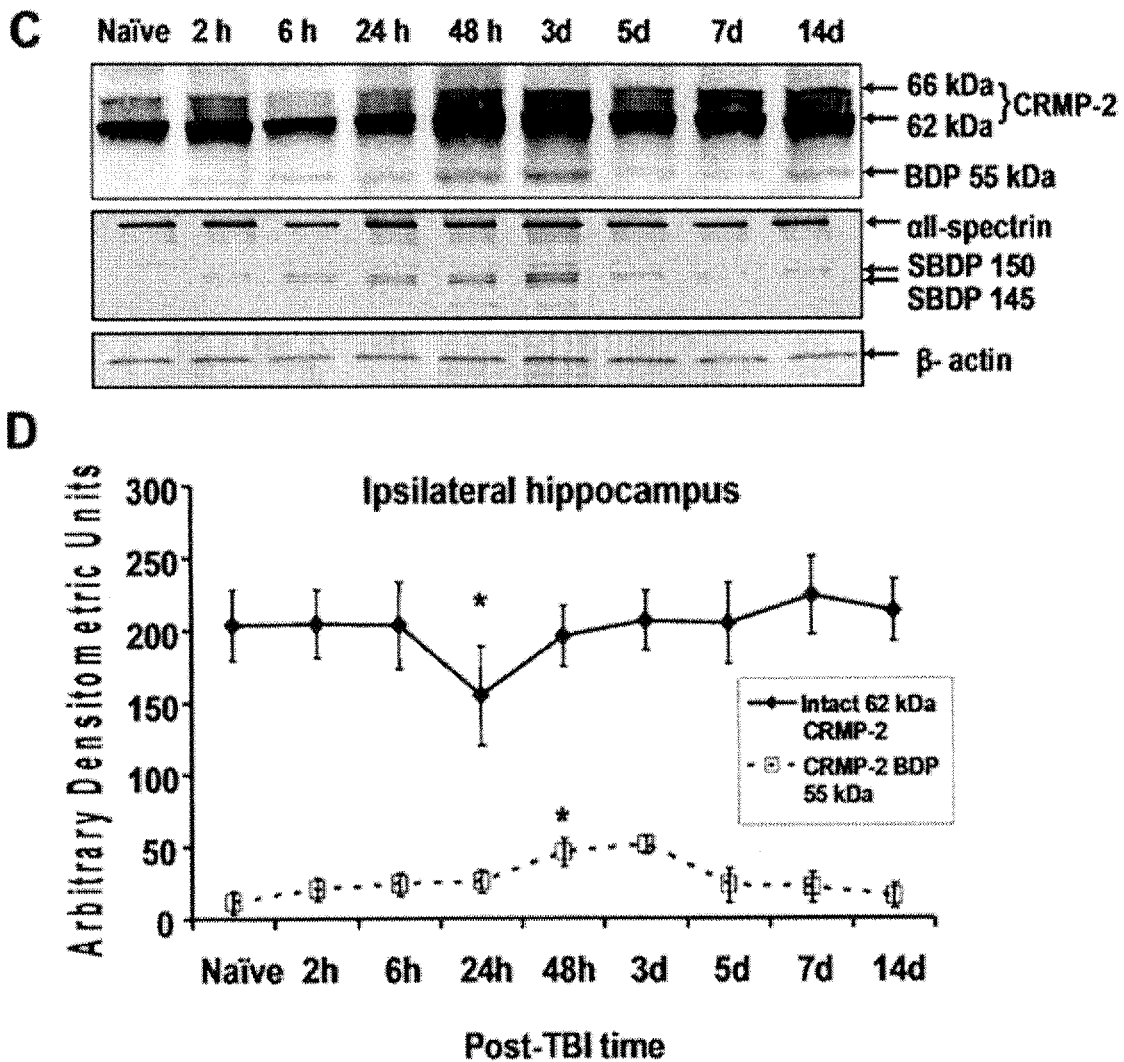

Spectrin proteolysis was used to correlate CRMP2 degradation with calpain and caspase activity (FIGS. 5A and 5C). Again, it was found that the formation of the SBDP150/145 calpain product strikingly paralleled the formation of the 55 kDa CRMP-2 BDP, demonstrating that CRMP2 proteolysis correlated with the calpain activity over time after TBI.

Example 4

CRMP2 Proteolysis Following TBI

Figure 2:
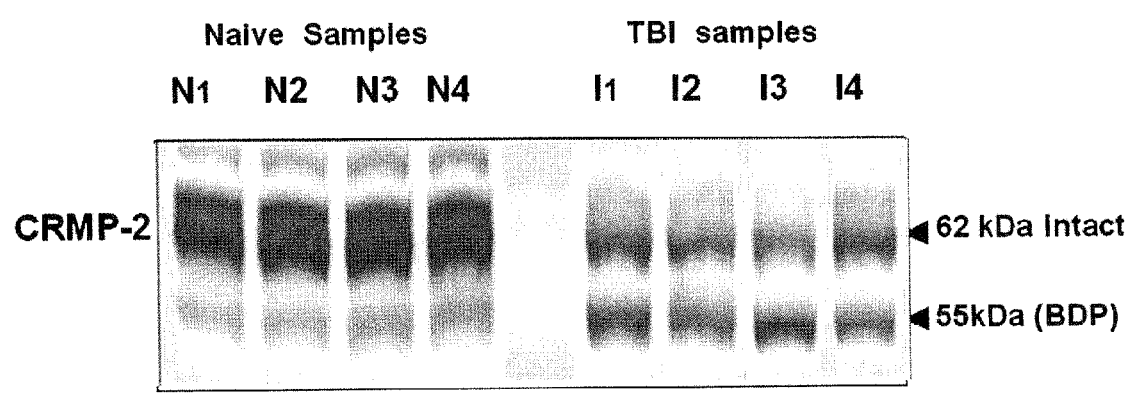
FIG. 2 is a Western blot showing CRMP-2 degradation in rat hippocampus 48 hr after TBI induced by CCI.
Figure 3:
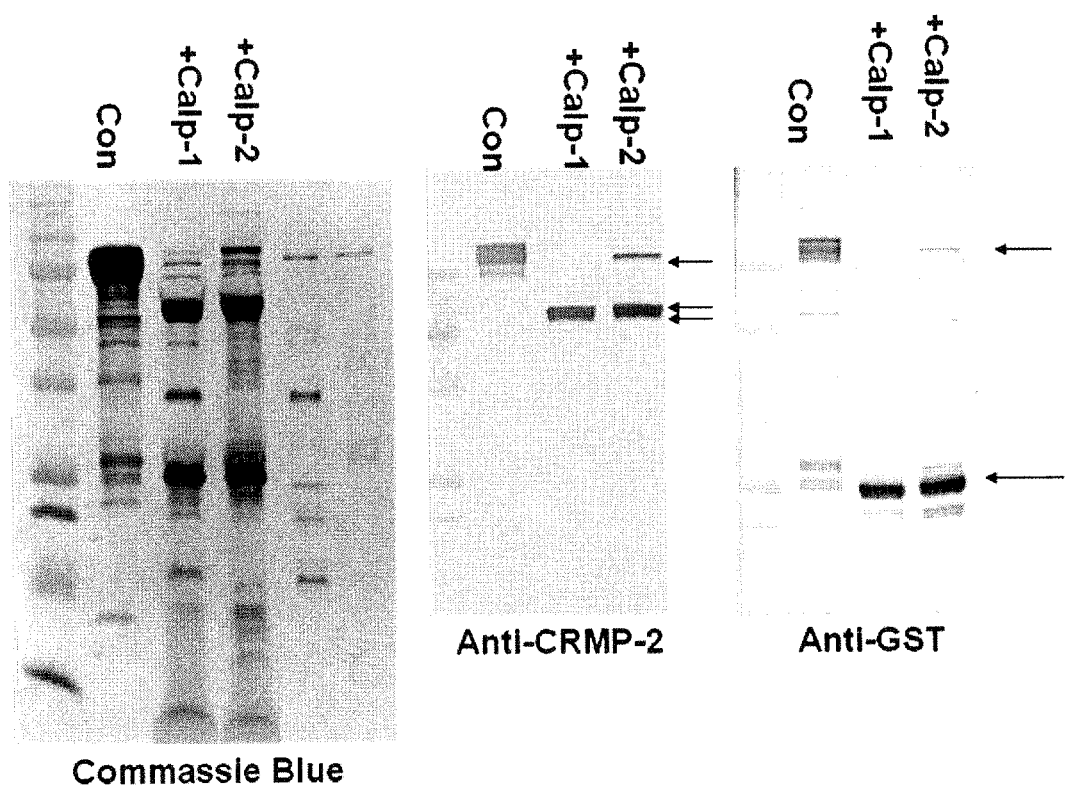
FIG. 3 is a Coomassie blot image (far left) and a Western blot (middle and right) of purified GST-CRMP-2 protein digested by Calpain. The obtained cleavage fragments were used to determine the calpain cleavage site.

This example was to determine whether CRMP2 proteolysis was calpain mediated following TBI, similar to the proteolysis found in cell culture after neurotoxin treatment. As shown in FIG. 2, in vitro calpain treatment of naïve brain lysate resulted in the same fragmentation pattern observed after TBI in vivo, with the 62 kDa and 66 kDa intact CRMP-2 bands disappearing. Pretreatment of the naïve lysate with calpain inhibitor (SJA6017) blocked formation of the 55 kDa CRMP-2 BDP, and preserved the 62 kDa CRMP2 bands. In contrast, caspase-3 treatment did not produce the 55 kDa BDP, though the 66 kDa intact CRMP2 band did completely disappear, even after applying the caspase inhibitor Z-VAD. The complete inhibition of calpain and caspase activity was confirmed by parallel monitoring of calpain and caspase associated αII-spectrin degradation. This was confirmed by using Phoretix 1D-gel imaging software to show that the molecular weight of the calpain mediated CRMP2 proteolytic product matched that of the 55 kDa BDP observed post-TBI in vivo. Therefore, calpain produced the 55 kDa CRMP-2 BDP, while caspase-3 was ruled out. The data provided evidence that CRMP2 proteolysis is due to calpain activation following TBI.

Example 5

Time Course of Changes of CRMP2 Levels in Brain

Figure 6A:
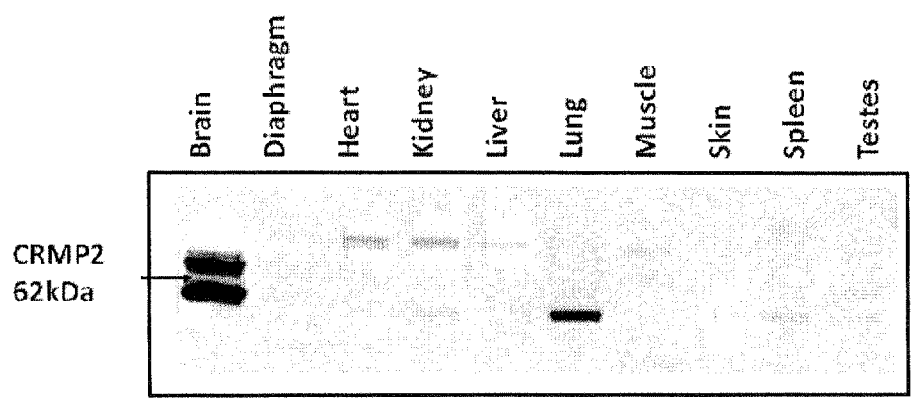
FIGS. 6A-6B.
Figure 6B:
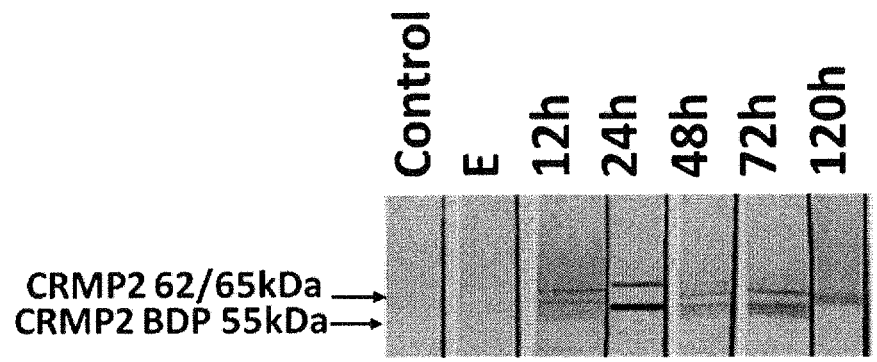

The time changes in naïve and TBI ipsilateral cortex and hippocampus tissue for intact CRMP2 are shown in FIGS. 5A-D up to 14 days post injury. FIG. 6A shows that significant amount of intact CRMP2 are found in brain tissue with lesser amounts in lung and no detectable amounts in other tissues. FIG. 6B shows that there is a reappearance of CRMP2 after about 12-24 hours from TBI.

Example 6

Synaptotagmin-1 Proteolysis Following TBI

Figures 14A, 14B:
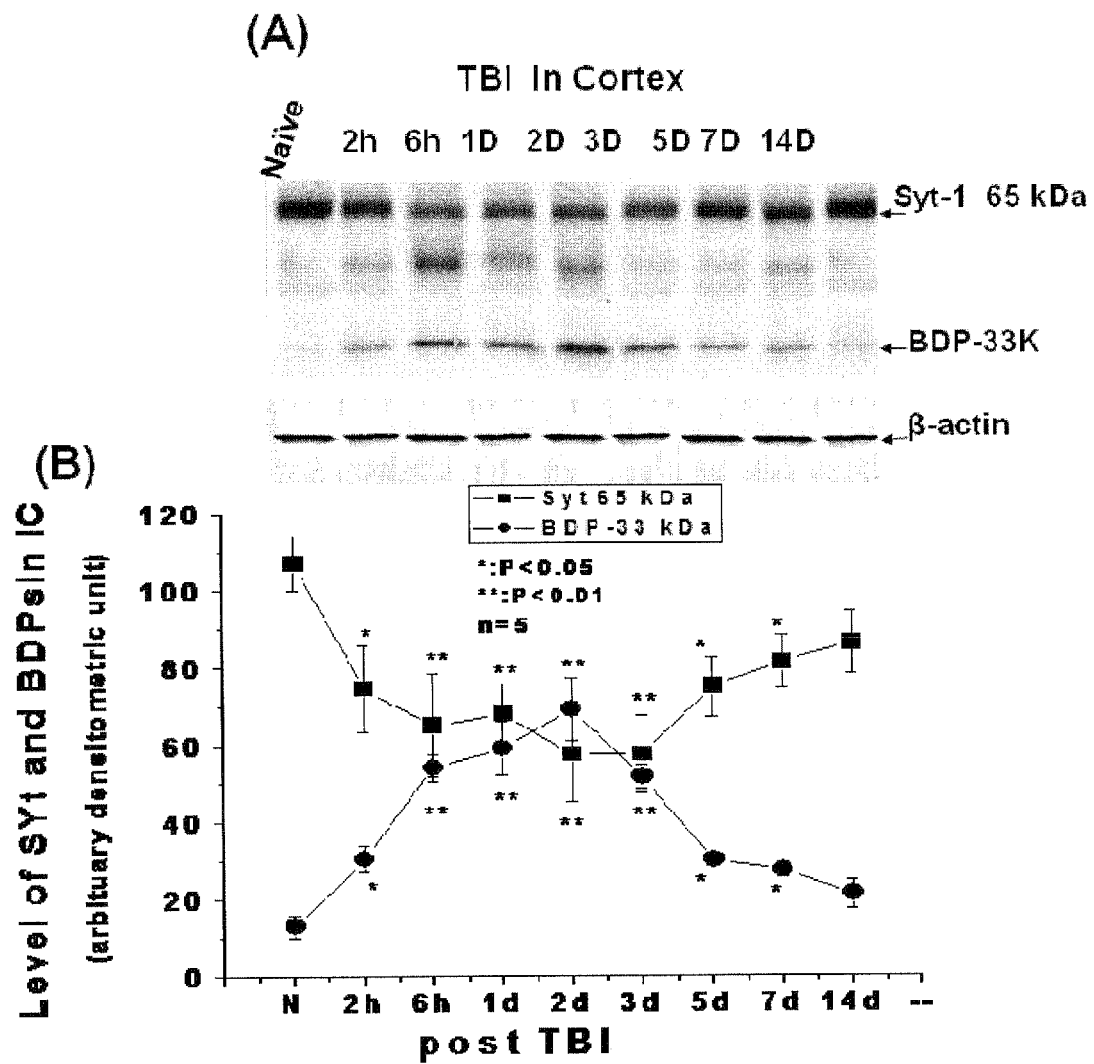
FIGS. 14A-14B.
Figures 15A, 15B:
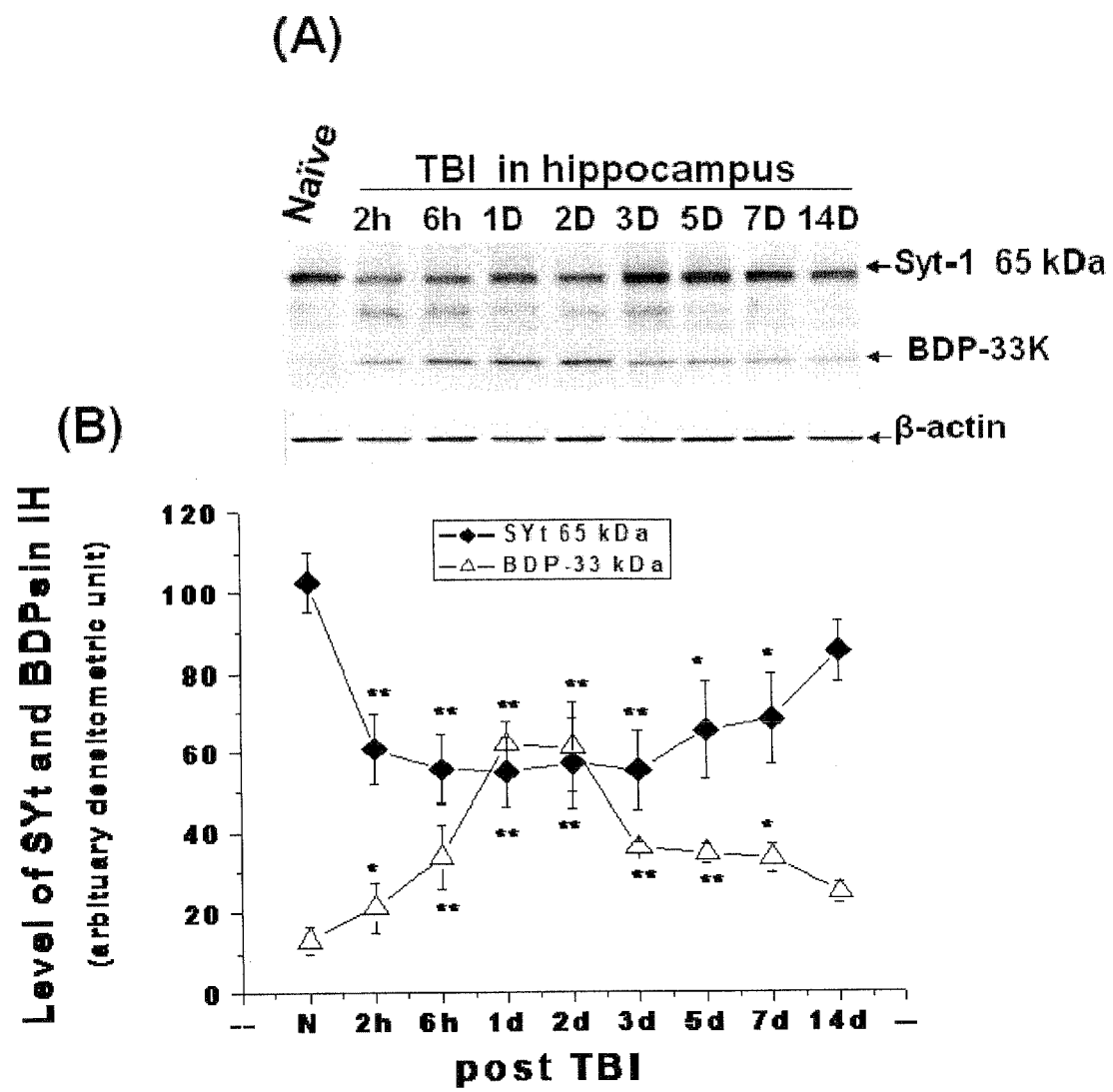
FIGS. 15A-15B.

Immunoblotting analysis with monoclonal synaptotagmin-1 antibody (BD, Cat # 610434) was employed to detect the N-terminal synaptotagmin-1 isoform. Western blot results showed that, when compared to naïve group, the Syt-1 65 kDa was extensively degraded into smaller fragment (BDP-33k) in the ipsilateral cortex (FIGS. 14A and 14B) and hippocampus (FIGS. 14C and 14D) at 48 hours after CCI but Syt-1 was not degraded in the naïve and sham groups.

No degradation of Syt-1 was observed in contralateral cortex and hippocampus samples. The integrity of Syt-1 in a post-TBI time course showed that in the ipsilateral cortex, 65 kDa Syt1 was significantly diminished as early as at 2 hours after TBI, and reached the lowest level at 48 hour after which the levels significantly recovered by 14 days after TBI.

N-terminal Syt-1 breakdown products (BDP-33k) accumulated in rat cortex beginning at 2 hrs and peaked at 48 hrs before approaching basal levels again in 7-14 days. Similarly, in the ipsilateral hippocampus, levels of Syt-1 isoform diminished at 2 hrs to 3 days and recovered at 14 days while Syt1 BDP-33k accumulated beginning at 2 hrs peaked at 24-48 hrs before approaching basal levels again in 14 days. Beta-actin blots were also performed routinely as protein loading evenness controls, thus ruling out technical artifacts.

Figure 9:
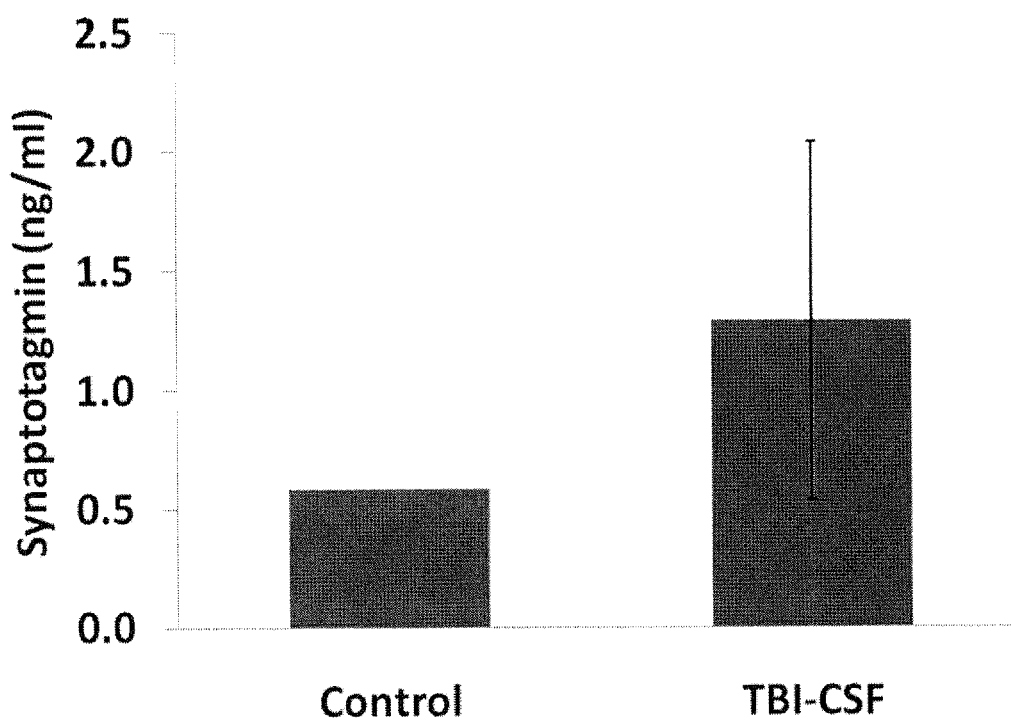
FIG. 9 is a graph showing the level of synaptotagmin in human CSF after TBI compared to normal control levels in an uninjured subject. Analysis was performed by a Syt-1 BDP-specific ELISA. The synaptotagmin cleavage site was identified between LG111*K112. Syt-1 BDP-specific antibodies can be generated against peptide NH$_2$-K112 TMKDQALKD (SEQ ID NO:1) (anti-Syt-1-BDP) or in close proximity, respectively. These antibodies can be combined with another antibody against the C' fragment to form a sandwich ELISA.

Synaptotagmin was found in human CSF, increasing at least 2-fold after TBI (FIG. 9) At least one calpain cleavage site is found near the N-terminus of Syt1 between glycine 111 and lysine 112 in LGKTMKDQALKD (SEQ ID NO:2), which produces a 19 kDa and a 46 kDa breakdown product. An additional cleavage site may occur between 149 and 150 leading to a 20 kDa and 35 kDa cleavage products. Anti-Syt-1 antibody (BD#610433) detects intact Syt-1 and the 35 kDa BDP while anti-Syt1-BDP (FIG. 16) detects the 20 and 46 kDa BDPs arising from calpain-2 cleavage. The anti-Syt1 antibody detects the intact 65 kDa synaptotagmin. Neither antibody detects BDPs from caspase-3, except for detection of the intact protein with anti-Syt1 (see FIG. 13).

Figure 10:
FIG. 10 is tissue specificity of Synaptotagmin1 as shown on a human tissue panel screen. 20 ug of homogenized human organ specific tissue was separated on a SDS-PAGE gel. Synaptotagmin1 specific antibody was used to screen the blot. The protein is very specific for brain tissue and has no cross reactivity with other tissue. This indicates that the SW ELISA, using this antibody would be very brain specific. Mouse anti-SYPT1 (USBiologicals S9109-22) @ 1:1000 dilution was used to probe the blot. 1=MW marker, 2=brain, 3=diaphragm, 4=heart, 5=kidney, 6=liver, 7=lung, 8=muscle, 9=skin, 10=spleen, 11=testes, 12=GST-Syt1(72 kDa) as +control).
Figure 17:
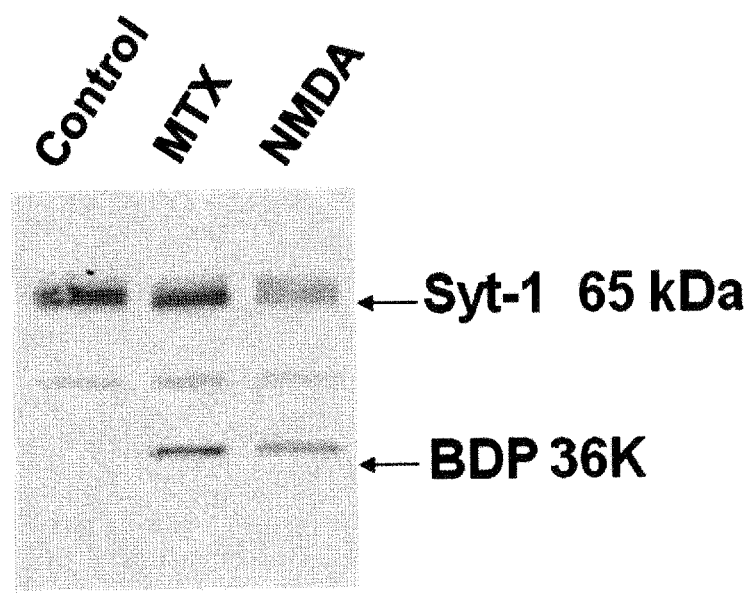
FIG. 17 is a Western blot of cell culture lysate probed with anti synaptotagmin antibody in a cell culture after treatment with MTX and NMDA.
Figure 18:
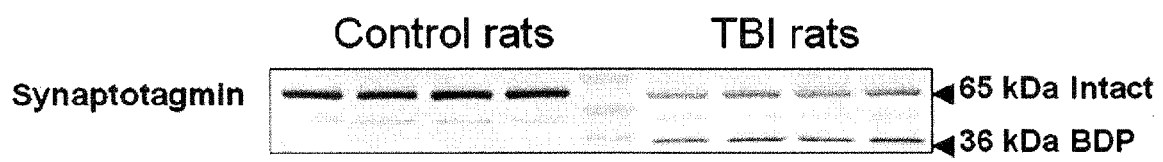
FIG. 18 is a Western blot of brain lysate probed with anti synaptotagmin antibody in rat brain tissue comparing and control and TBI.

Synaptotagmin is specific for brain (FIG. 10). Western blot showed a 65 kDa band from rat tissue lysates run on gel probed with mouse anti-sypt1 (USB S9109-22) and a small 36 kDa band (FIG. 17). Other tissues, including diaphragm, heart, kidney, liver, lung, muscle, skin spleen and testes did not show any bands when probed with the antibody.

Example 7

Novel Syt-1 Fragment-Specific Antibodies

Figure 13:
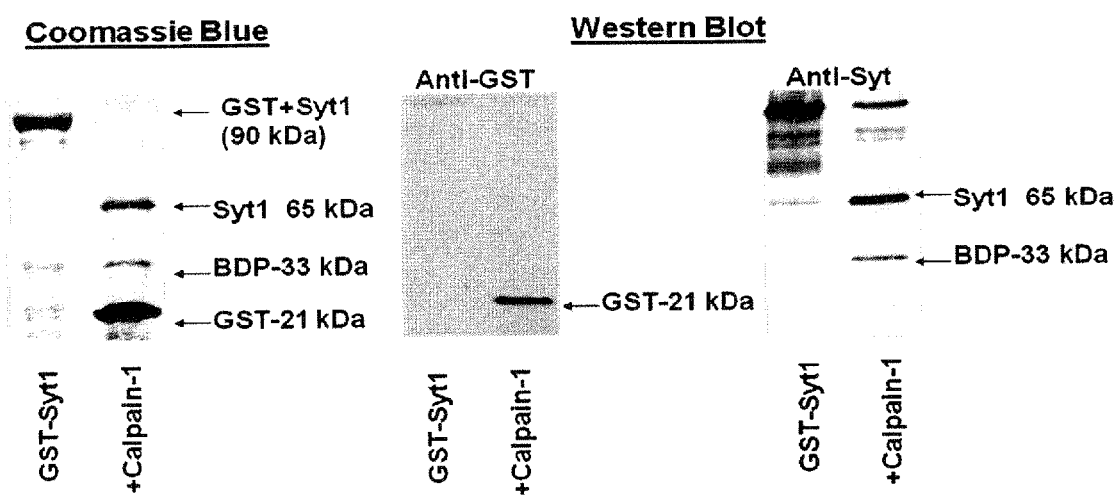
FIG. 13 shows GST-synaptotagmin digestion by calpain. The recombinant synaptotagmin was cleaved in vitro to a 21 kDa BDP as detected with anti-GST. Both the 65 kDa (intact protein) and 33 kDa BDP were detected with anti-Syt. The N-terminal BDP-33K band (A) was micro-sequenced to determine the cleavage site.
Figure 16:
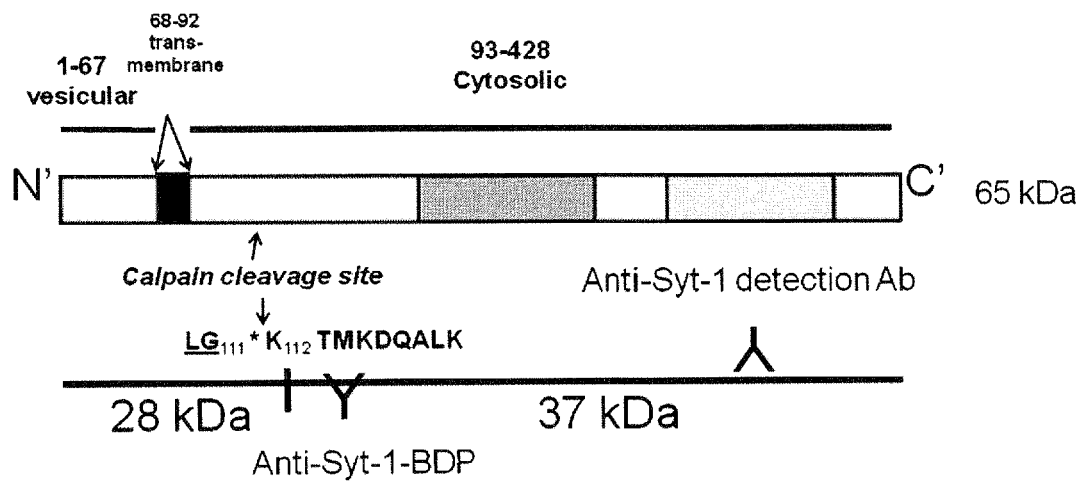
FIG. 16 is a cartoon showing the vesicular and transmembrane regions of regions of synaptotagmin1. The amino acid sequence of the calpain cleavage site is shown between position 111 and 112 providing a 28 kDa and 37 kDa breakdown products. Detection of the 37 kDa fragment by anti-Syt-I and the anti-Syt-1 BDP is shown.

A 9-residue peptide (KTMKDQALK, SEQ ID NO:3) was designed based on the Identification of synaptotagmin-1 cleavage site by N-terminal micro-sequencing (FIG. 16). The peptide was conjugated to carrier protein KLH and injected into both rabbits and mice. Animal sera were antigen affinity-purified using the same peptide-coupled resin. The purified anti-Syt-1 33 kDa BDP antibody was tested against naïve and TBI cortical samples. Anti-Syt1-BDP-33k strongly detected the Syt1-BDP-33k fragment only. Unlike the total Syt1-antibody (BD, Cat # 610434), this fragment-specific antibody did not detect intact Syt-1 band (FIG. 13).

Example 8

Changes in CRMP2 and Syt and BDPs after TBI

The relative changes in CRMP2 with respect to its BDPs was measured in human CSF over a period of 7 days. FIG. 6B is a Western blot analysis of human control and TBI CSF collected at different time points, CRMP2 has a molecular weight of 65 kDa. The full length protein is seen in brain lysate at 62 kDa with a BDP at 55 kDa. Bands are seen in TBI CSF from time of patient admission (E) up to 5 days. Control CSF shows only a low level of intact protein. BDP is detected in large amounts 12 hours post injury (measurements made at time of admission, 12 hr, 24 hr, 48 hr, 72 hr and 120 hr post injury). The blot was probed using mouse anti-CRMP2 (IBL Cat# 11096).

Figure 11:
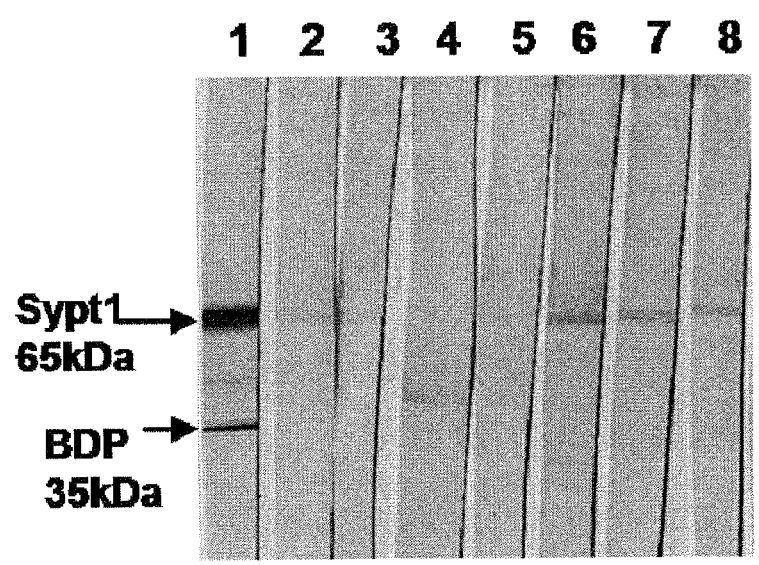
FIG. 11 is a Western blot analysis of human control and TBI CSF collected at different time points showing Synaptotagmin1. Synaptotagmin1 has a molecular weight of 65 kDa. The Full length protein is seen with the brain lysate at 65 kDa. The BDP is also seen at 35 kDa. Bands are seen with the TBI CSF from enrollment of the patient (3) to 120 hrs (8). Control CSF (2) shows only low level of intact protein. BDP is detected at large amounts 12 h post injury (4). Rat brain (1), CSF control (2), Enrollment of patient (3), 12 h (4), 24 h (5), 48 h (6), 72 h (7), 120 h (8) post injury.
Figure 12:
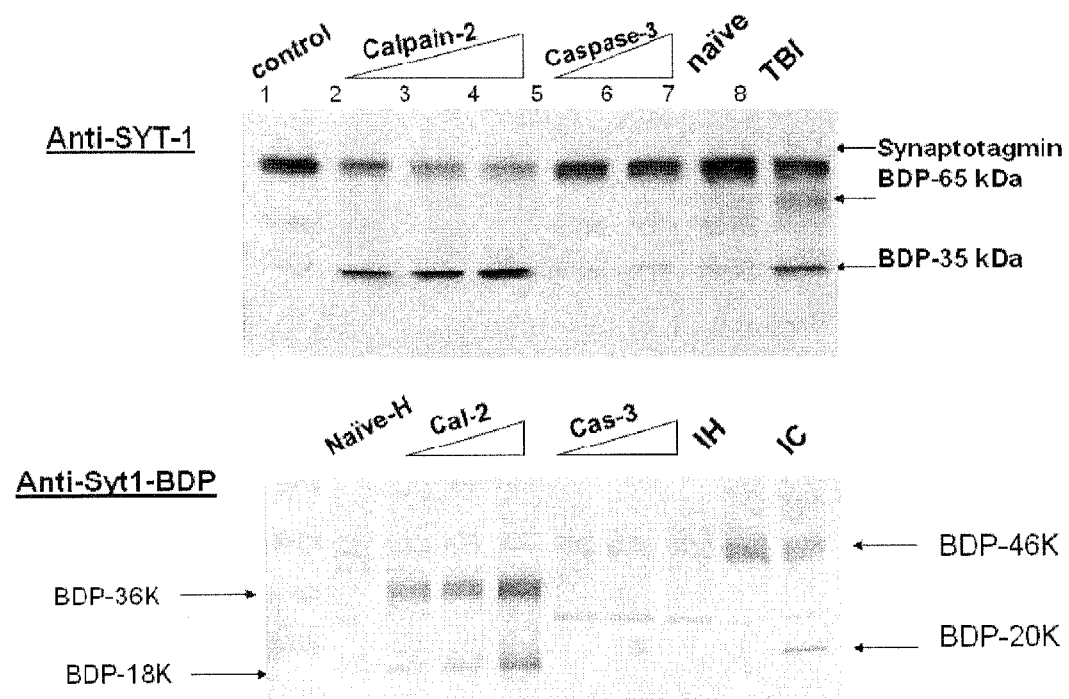
FIG. 12 showed that there a Syt-BDP-35k in lysate digested by calpain-2, but not in digested caspase-3 and in control cell lysates. Comparing Naïve and TBI brain lysate reveals a similar pattern of full length Syt (65 kDa) and Syt BDP (35 kDa). The top blot was probed with a commercial anti synaptotagmin antibody, whereas the bottom blot was probed with our unique anti-Syt-BDP antibody, which was generated against the $K_{112}$ TMKDQALK (SEQ ID NO:1) sequence. Only Syt BDPs are detected with that antibody and not full length protein.

Similar changes were measured for synaptotagmin1. Western blot analysis of human control and TBI CSF were collected at different times, FIG. 11. Synaptotagmin1 has a molecular weight of 65 kDa. The BDP is also seen at 35 kDa (FIG. 12). Bands are seen with the TBI CSF from enrollment of the patient (3) up to 120 hr (5 days), see 8 in FIG. 11. Control CSF (2) shows only a low level of intact protein. BDP is detected in large amounts post injury (4). Rat brain (1), CSF control (2), Enrollment of patient (3), 12 hr (4), 24 hr (5), 48 hr (6), 72 hr (7) and 120 hr (8) post injury.

The lysate of cerebrocortical cultures and the lysate of naïve hippocampus (containing intact Syt-1) were subjected to various protease treatments in vitro in order to identify what protease is responsible for the in vivo Syt1 cleavages observed following TBI in rat brain. The lysate was exposed to various amounts of calpain-2 (different substrate: protease ratio). The treated lysate samples were then analyzed by Western blots probed with anti-αII-spectrin and anti-total Syt-1, respectively. αII-spectrin blot revealed dose-dependent reduction of intact protein and formation of the characteristic BDP of 150 and 145 kDa (SBDP150 and SBDP145) Syt1-blot also showed a calpain-concentration-dependent reduction of intact Syt1. Calpain treatment also produced a BDP identical to the 33 Syt1-fragment produced following TBI.

Digestion with calpain-1 showed identical results (data not shown). To ascertain that the calpain-produced Syt1-fragment contains the novel N-terminal (KTMKDQALK, SEQ ID NO:3) observed in vivo, the fragment-specific antibody was applied to these samples and confirmed that its cross-react with the calpain produced Syt1-fragment.

Since caspase-3 is activated in apoptosis after neuronal injury, the sensitivity of Syt1 to caspase-3 digestion was tested. The results show that while αII-spectrin was degraded to the characteristic SBDP150i and SBDP120, Syt1 was resistant to caspase-3 in the same samples, using total Syt1- and Syt1-fragment-specific antibodies. The sensitivity of Syt1 to various amounts of cathepsin B, cathepsin D, MMP-2, and MMP-9 was further analyzed. Overall, Syt1 was relatively resistant to these proteases and under no conditions were the TBI-associated characteristic BDP-33k detected (results not shown).

The degradation of CRMP1, 2, and 4 after acute neuronal injuries by in vivo TBI and in vitro glutamate excitotoxicity is shown in the above examples. The data demonstrate that CRMP1, 2 and 4 are proteolyzed after neurotoxic injury and TBI. Additionally, the decrease of intact CRMP-2 occurs with a concurrent increase of a 55 kDa CRMP2 fragment due to calpain proteolysis, in vitro and in vivo, and the calpain-mediated CRMP2 proteolysis appears to associate with neuronal cell injury and neurite damage.

CRMP2 was proteolyzed to a 55 kDa BDP under two calpain-dominant challenges (MTX and NMDA) and with the apoptotic inducer STS in cortical neuron. The decrease of the intact CRMP-2 and increase of CRMP2 55 BDP following NMDA treatment were strikingly paralleled NMDA induced neuronal cell death over time. In addition to attenuation of cell death induced by NMDA treatment within 6 hour, pretreatment of primary cortical culture with the cell-permeable calpain-inhibitor SJA, not the caspase inhibitor Z-VAD, prevented the formation of the 55 kDa CRMP2 BDP, preserving the intact 62 kDa CRMP-2 protein. Furthermore, calpain inhibition prevented redistribution of CRMP2 from neurites to the cell body, and preserved the architecture of neurites. These data indicated that CRMP2 has a proteolysis link to calpain mediated neurite degeneration.

In addition to LDH assay, other methods such as 3-(4,5-dimethylthiazol-2-yl)2,5-diphenyl-tetrazolium bromide (MTT) assay, TUNEL assay, Hoest and propidium iodide (PI) PI staining can be used to concordantly assess neuronal cell death. Preincubating with calpain inhibitor (SJA6017) did not effectively protect neurons from excitotoxic injury after 12 hours. Thus in addition to calpain, other pathways, such as calmodulin, phospholipase, protein kinase A might also contribute to the excitotoxic neuron death.

Proteolysis of CRMP2 was only exhibited in injured brain regions with the formation of the CRMP2 55 kDa BDP in correlation with calpain activation over time following TBI. The apparent rebound of CRMP2 by day 5 after TBI may be due to loss of necrotic tissue, thus leaving behind the remaining more intact and/or recovering tissue for sampling. Treatment of naïve brain lysate with purified calpain, but not caspase, resulted in a 55 kDa cleavage product identical to that observed after TBI. The data demonstrate that calpain mediated CRMP2 proteolysis occurs, and appears to link in time to neuronal cell injury and neurite damage after excitotoxic injury.

Both calpain and caspase treatment resulted in the disappearance of the 66 kDa CRMP2 band, whereas only calpain treatment induced formation of the 55 kDa CRMP-2 BDP. Previous studies have shown that the 66 kDa CRMP2 is a phosphorylated form of CRMP2 while the 62 kDa form was unphosphorylated. Others have demonstrated that, following incubation of brain lysate with EGTA, the 66 kDa CRMP2 was dephosphorylated to the 62 kDa CRMP2 form. Since the caspase digestion buffer used in the studies eported here contained 5 mM EGTA and 5 mM EDTA, the disappearance of the 66 kDa CRMP2 band following caspase-3 treatment was likely due to dephosphorylation, which could not be prevented by pan-caspase inhibition.

CRMP2 has two domains; one is a dihydropyrimidinase (DHPase) domain (residues 64-413), the other is a C2 domain (residues 486-533) following SBASE analysis. Even though CRMP2 has high sequence similarity to DHPase, it has no known enzyme activity (hydrotoinase or dihydrophrimidinase). Important phosphorylation sites are located within the C2 portion or CRMP2.

Figure 4:
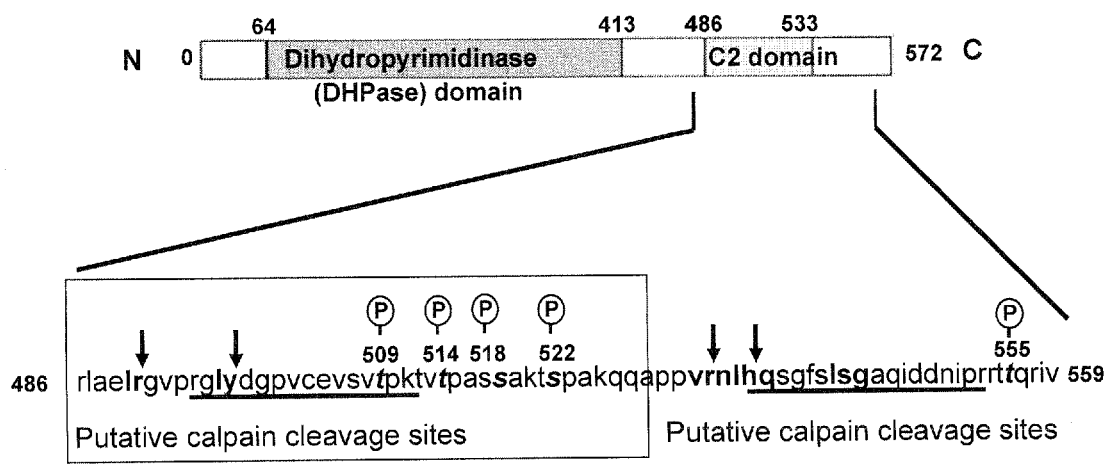
FIG. 4 shows a sequence analysis of CRMP2 and potential calpain cleavage site assignment (SEQ ID NO: 18). The top panel shows the domain architecture of CRMP-2. The bottom of the figure depicts a schematic representation of residues 486-559 toward the C-terminus of CRMP2. PEST regions are underlined. Arrows indicate putative calpain cleavage sites, two of which (first and third from the left) have been observed by mass spectrometry.

Sequence analysis revealed multiple putative cleavage sites for calpain on the C-terminus of CRMP2 (FIG. 4) with the preferred residues Leu, Thr and Val in position P2, and Lys, Tyr and Arg in position P1. The epitope used to generate the C4G antibody is also shown (residue 486 to 528). Another C terminal antibody was used with an epitope from residue 551-559 to narrow down the possible cleavage site forming the 55 kDa CRMP2 BDP. With this antibody, the intact CRMP2 was shown to decrease following excitotoxic treatment and TBI, but the BDP 55 kDa was not observed (data not shown), indicating that the cleavage site is located between residue 486 and 551.

There are also two PEST regions (residues 496-511 and 535-552) located on the C-terminal end of CRMP2 (residues 486-559) as identified by PESTfind analysis). PEST regions tend to depict regions of rapid degradation in proteins. The first PEST region RGLYDGPVCEVSVTPK (SEQ ID NO:9) (residues 496-511 of SEQ ID NO:7) contains preferred calpain cleavage site $Leu_{498}$-$Tyr_{499}$-Asp. Furthermore, cleavage at residue 499 results in a truncated CRMP-2 with a theoretical mass 54.7 kDa, which matches the experimental mass of 55 kDa for the CRMP-2 BDP. The other putative calpain-cleavage sites shown in also meets the criteria of the calpain digestion, but the theoretical fragment mass is bigger than the observed 55 kDa BDP. Thus, by analyzing the sequence and the experimental data, the calpain cleavage site was identified as between residues $LY_{499} \downarrow D_{500}$ in CRMP-2.

An important function of CRMP2 is its involvement in axonal regeneration or elongation. Over-expression of CRMP2 induces the formation of multiple axons and primary axon elongation.

Besides CRMP2, the present work shows that CRMP-1 and CRMP-4 are also degraded after neuronal injury and TBI. Until now, there has been no report on the degradation of CRMP-1 following neurotoxic injury or TBI. Although all CRMP isoforms share some homology, CRMP-1 and 4 exhibit somewhat higher identity with each other (68-75%), while CRMP-5 has relatively low identity with the rest of family members (49-50%). Thus, CRMP-5 might best be classified into a different subfamily, which may explain why it was not found to be sensitive to calpain proteolysis after TBI.

Example 9

Synaptotagmin-1 BDP Epitopes for Antibody Production and Sandwich ELISA Development As shown in FIG. 16, the Synaptotagmin-1 (Syt-1) major cleavage site is in the epitope $AINMKDVKDLG^{111}$ * $K^{112}TMKDQALKD$ (SEQ ID NO:4), (*-designed cleavage sites by calpain), as such that AINMKDVKDLG—$_{COOH}$(SEQ ID NO:5), which can be used to make N-terminal half Sypt-1 fragment-specific antibody. $_{NH2}$-KTMKDQALK (SEQ ID NO:3), can be used to make C-terminal half Sypt-1 fragment-specific antibody. Additional antibodies can be raised to complement these fragment-specific antibodies to make sandwich ELISA for synaptotagmin-1 detection.

Example 10

CRMP Breakdown Product (BDP) Epitopes for Antibody Production and Sandwich ELISA Development Examples of calpain cleavage products in human CRMP-2 between amino acids 483-559: KARSRLAELRGVPRG-LYDGPVCEVSVTPKTVTPASSAKTSPAKQQA PPVRN-LHQSGFSLSGAQIDDNIPRRTTQRIV (SEQ ID NO: 7), the calpain cleavage region, include KARSRLAELR$_{492}$*G$_{493}$VPRGLYDGP (SEQ ID NO:8); LRGVPRGLY$_{499}$*D$_{500}$GPVCEVSVT (SEQ ID NO:9); TPKTVTPAS$_{517}$*S$_{518}$AKTSPAKQQAPP (SEQ ID NO:10) (*-designed cleavage sites by calpain).

To detect N-terminal larger CRMP-2 BDP, one can generate antibodies against peptides with a new COOH terminal: KARSRLAELR—$_{COOH}$ (SEQ ID NO:11); LRGVPRGLY—$_{COOH}$ (SEQ ID NO:12); or TPKTVTPAS—$_{COOH}$ (SEQ ID NO:13).

The region upstream from these sites, such as amino acid positions 454-465 LEDGTLHVTEGS (SEQ ID NO:14), generates a second antibody to make sandwich ELISA for N-terminal CRMP-2 large BDP detection. To detect C-terminal smaller CRMP-2 BDP, one can generate antibodies against peptides with a new —NH$_2$ terminal: $_{NH2}$-GVPRG-LYDGP (SEQ ID NO:15); $_{NH2}$-DGPVCEVSVT (SEQ ID NO:16) and; $_{NH2}$-SAKTSPAKQQAPP (SEQ ID NO:17).

The C-terminal region sequence (e.g., PGGRANITSLG, SEQ ID NO:6), downstream from these sites can be used to generate a second antibody to make a sandwich ELISA for CRMP-2 C-terminal small BDP.

CRMP-2 swELISA detects a range of 0.070 ng to 50 ng target, see FIG. 7. Such a CRMP-2 sandwich ELISA detects CRMP2 BDP levels in human CSF elevated to 12-17 ng/mL at 12, 24, 48 and 72 h after traumatic brain injury compared to undetectable levels in controls, similar to the results shown in FIG. 11.

Synaptotagmin-1-swELISA detects a range of 0.069 ng to 50 ng target, see FIG. 8. Such a Sypt-1 sandwich ELISA can detect Synaptotagmin-1 BDP levels at 24, 48 and 72 h after TBI in human biofluid (CSF) elevated to 1.5-14 ng/mL versus 0.5 ng/mL in controls, see FIG. 9.

What is claimed is:

1. A method of determining the presence of trauma induced brain injury, comprising:
   collecting a biological sample from an injured subject suspected of having the trauma induced brain injury, wherein the biological sample is blood or cerebral spinal fluid (CSF);
   measuring said sample for an amount of at least one biomarker of collapsin response mediator protein-1, -2, -3, -4, or -5 (CRMP), synaptotagmin or at least one CRMP breakdown product (BDP) or synaptotagmin BDP formed by the trauma induced brain injury;
   comparing the amount of the biomarker CRMP or synaptotagmin with an amount of CRMP or synaptotagmin in an uninjured subject, wherein a decreased amount of the CRMP or the synaptotagmin from said injured subject compared with the uninjured subject is indicative of trauma induced brain injury in said injured subject; or
   comparing the amount of the biomarker CRMP BDP or synaptotagmin BDP with an amount of the respective BDP in an uninjured subject, wherein synaptotagmin BDP is one or more proteins produced by calpain cleavage between a glycine-lysine (G-K) in the synaptotagmin and wherein the CRMP BDP is one or more proteins produced by calpain cleavage between one or more of serine-serine (S-S), Leu-Tyr (L-Y), tyrosine-aspartic (Y-D) or arginine-glycine (R-G), wherein an increased amount of the CRMP BDP or the synaptotagmin BDP, as compared with the respective amount in the uninjured subject, is indicative of the trauma induced brain injury.

2. The method of claim 1 wherein the measured CRMP is CRMP-1, CRMP-2, CRMP-4, or CRMP-5.

3. The method of claim 1 further comprising collecting successive biological samples and monitoring the amount of the biomarker measured in the biological sample of the injured subject from time of injury to a time when the amount of the biomarker measured in a successive biological samples of the injured subject substantially equals the amount of the biomarker measured in an uninjured subject, wherein recovery of the injured subject is indicated when the amount of the biomarker approaches the amount of the biomarker measured in the uninjured subject.

4. The method of claim 1 wherein the measured biomarker is the CRMP-2 with a molecular weight of 62kDa or 66kDa whereby a decrease of the biomarker in the injured subject with respect to the uninjured subject is indicative of trauma induced brain injury.

5. The method of claim 1 wherein the measured biomarker is a CRMP-4 BDP with a molecular weight of 58kDa whereby an increase of the biomarker in the injured subject with respect to the uninjured subject is indicative of trauma induced brain injury.

6. The method of claim 1 wherein the measured biomarker is one or more BDPs of synaptotagmin with a molecular weight of 35 kDa, 20 kDa or 46 kDa whereby an increase of the biomarker in the injured subject with respect to the uninjured subject is indicative of trauma induced brain injury.

7. The method of claim 1 wherein the measured biomarker is a CRMP-2 BDP with a molecular weight of 55kDa whereby an increase of the biomarker in the injured subject with respect to the uninjured subject is indicative of trauma induced brain injury.

8. The method of claim 1 wherein said sample is measured for an amount of at least two biomarkers of a collapsin response mediator protein (CRMP), synaptotagmin or a BDP of CRMP or synaptotagmin formed by the trauma induced brain injury.

9. The method of claim 8 wherein the first biomarker is a CRMP and the second biomarker is a BDP of the CRMP.

10. The method of claim 9 wherein a decreased amount of the CRMP and an increased amount of the CRMP BDP from said injured subject, as compared with the uninjured subject, is indicative of the trauma induced brain injury in said injured subject.

11. The method of claim 9 wherein the CRMP is CRMP-2 with a molecular weight of 62kDa or 66kDa and the CRMP BDP is CRMP-2 55kDa BDP whereby a decrease of CRMP-2 62 kDa or 66 kDa proteins and an increase of CRMP-2 55 kDa BDP in the injured subject with respect to the uninjured subject is indicative of trauma induced brain injury.

12. The method of claim 9 wherein the CRMP is CRMP-4 with a molecular weight of 62kDa and the CRMP BDP is CRMP-2 55kDa BDP whereby a decrease of CRMP-2 62 kDa or 66 kDa proteins and an increase of CRMP-2 55 kDa BDP in the injured subject with respect to the uninjured subject is indicative of trauma induced brain injury.

13. The method of claim 8 wherein the first biomarker is synaptotagmin and the second biomarker is a BDP of synaptotagmin.

14. The method of claim 13 wherein a decreased amount of the synaptotagmin and an increased amount of the synaptotagmin BDP from said injured subject, as compared with the uninjured subject, is indicative of the trauma induced brain injury in said injured subject.

15. The method of claim 14 wherein the synaptotagmin has a molecular weight of 65kDa and the synaptotagmin BDP is a 35 kDa, 20 kDa or 46 kDa BDP whereby a decrease of synaptotagmin 65kDa protein and an increase of 35 kDa, 20 kDa or 46 kDa BDP in the injured subject with respect to the uninjured subject is indicative of trauma induced brain injury.

* * * * *

UNITED STATES PATENT AND TRADEMARK OFFICE
CERTIFICATE OF CORRECTION

Page 1 of 2

PATENT NO. : 8,557,526 B2
APPLICATION NO. : 12/535960
DATED : October 15, 2013
INVENTOR(S) : Andrew K. Ottens et al.

It is certified that error appears in the above-identified patent and that said Letters Patent is hereby corrected as shown below:

In the Specifications

Column 1,
Line 14, "grant Pe" should read --grant #--.
Line 16, "N S40182" should read --NS40182--.

Column 2,
Line 22, "GSK-3-phosphorylated" should read --GSK-3b-phosphorylated--.

Column 3,
Lines 22-23, "products identified" should read --products were identified--.

Column 4,
Line 42, "72," should read --72h,--.

Column 5,
Line 14, "showed that there a" should read --shows that there is a--.
Line 53, "regions of regions of synaptotagmin1" should read --regions of synaptotagmin1--.

Column 6,
Lines 8-9, "comparing and control" should read --comparing control--.

Column 13,
Line 1, "repeated this 2 times" should read --repeated 2 times--.
Line 11, "Santa cruz" should read --Santa Cruz--.

Column 14,
Lines 46-47, "against a synthetic peptides" should read --against synthetic peptides--.

Signed and Sealed this
Eleventh Day of March, 2014

Michelle K. Lee
*Deputy Director of the United States Patent and Trademark Office*

CERTIFICATE OF CORRECTION (continued)
U.S. Pat. No. 8,557,526 B2

Column 15,
Line 14, "SEQ D NO:3)" should read --SEQ ID NO:3)--.

Column 16,
Line 20, "anti-phsopho-CRMP2" should read --anti-phospho-CRMP2--.

Column 20,
Line 47, "studies eported" should read --studies reported--.

Column 21,
Line 15, "sites shown in also meets" should read --sites also meet--.